(12) United States Patent
Reuter et al.

(10) Patent No.: US 11,072,573 B2
(45) Date of Patent: Jul. 27, 2021

(54) BINAPHTHYL COMPOUNDS

(71) Applicant: REUTER CHEMISCHE APPARATEBAU E.K., Freiburg (DE)

(72) Inventors: Karl Reuter, Freiburg (DE); Vasyl Andrushko, Freiburg (DE); Mark Kantor, Freiburg (DE); Florian Stolz, Freiburg (DE); Noriyuki Kato, Tokyo (JP); Mitsuteru Kondo, Tokyo (JP); Munenori Shiratake, Kamisu (JP); Kentaro Ishihara, Tokyo (JP); Shinya Ikeda, Tokyo (JP); Shoko Suzuki, Tokyo (JP); Koji Hirose, Tokyo (JP); Kensuke Oshima, Tokyo (JP); Shuya Nagayama, Tokyo (JP)

(73) Assignee: Reuter Chemische Apparatebau E.K., Freiburg (DE)

( * ) Notice: Subject to any disclaimer, the term of this patent is extended or adjusted under 35 U.S.C. 154(b) by 0 days.

(21) Appl. No.: 16/642,219

(22) PCT Filed: Aug. 29, 2018

(86) PCT No.: PCT/EP2018/073245
§ 371 (c)(1),
(2) Date: Feb. 26, 2020

(87) PCT Pub. No.: WO2019/043060
PCT Pub. Date: Mar. 7, 2019

(65) Prior Publication Data
US 2020/0354299 A1 Nov. 12, 2020

(30) Foreign Application Priority Data
Aug. 30, 2017 (EP) ..................................... 17188576

(51) Int. Cl.
C07C 43/23 (2006.01)
C08G 64/00 (2006.01)

(52) U.S. Cl.
CPC .................................... C07C 43/23 (2013.01)

(58) Field of Classification Search
CPC ................... C07C 43/23; C08G 64/06
See application file for complete search history.

(56) References Cited

U.S. PATENT DOCUMENTS 9,360,593 B2    6/2016 Ishizuka et al.
2016/0319069 A1  11/2016 Shigematsu et al.

FOREIGN PATENT DOCUMENTS

JP        2002332345 A    11/2002

OTHER PUBLICATIONS

Bourrain, S , et al., "Regioselective Rapid Analogue Syntheses of 1-Methyl-3,5-diarylpyrazoles via Palladium-catalysed Coupling to 3(5)-Pyrazolyl Nonaflates", Synlett 5, 795-798 (2004).

Bunzen, J , et al., "Synthesis and Helicate Formation of a New Family of BINOL-Based Bis(bipyridine) Ligands", J Am Chem 131(10), 3621-3630 (2009).

Egami , et al., "Iron-Catalyzed Asymmetric Aerobic Oxidation: Oxidative Coupling of 2-Naphthols", J Am Chem Soc 131(17), 6082-6083 (2009).

Ema, T , "Synthesis and Evaluation of Chiral Selectors with Multiple Hydrogen-Bonding Sites in the Macrocyclic Cavities", J Org Chem 75(13), 4492-4500 (2010).

Lee, C , et al., "Carbon—carbon-linked (pyrazolylphenyl)oxazolidinones with antibacterial activity against multiple drug resistant gram-positive and fastidious gram-negative bacteria", Bioorg Med Chem Lett 9, 3243-3253 (2001).

Li, Y , et al., "A Protecting-Group-Free Route to Chiral BINOL—Phosphoric Acids", Europ J Org Chem, 3932-3937 (2011).

Nie, Z , et al., "Structure-Based Design, Synthesis, and Study of Potent Inhibitors of β-Ketoacyl-acyl Carrier Protein Synthase III as Potential Antimicrobial Agents", J Med Chem 48(5), 1596-1609 (2005).

(Continued)

*Primary Examiner* — Sikarl A Witherspoon
(74) *Attorney, Agent, or Firm* — Viksnins Harris Padys Malen LLP

(57) ABSTRACT

The present invention relates to binaphthyl compounds of the formula (I), which are suitable as monomers for preparing polycarbonate resins having beneficial optical properties and which can be used for producing optical lenses: Formula (I) where X is $C_2$-$C_4$-alkandiyl or $C_1$-$C_4$-alkandiyl-C(O)—, where C(O) is bound to the oxygen atom of the hydroxyl group and where $C_2$-$C_4$-alkandiyl or $C_1$-$C_4$-alkandiyl, respectively, are unsubstituted or carry a phenyl ring; R and R' are identical or different and selected from mono or polycyclic aryl having from 6 to 36 carbon atoms and mono- or polycyclic hetaryl having a total of 5 to 36 atoms, which are ring members, where 1, 2, 3 or 4 of these atoms are selected from nitrogen, sulfur and oxygen, while the remainder of these atoms are carbon atoms, where mono- or polycyclic aryl and mono- or polycyclic hetaryl are unsubstituted or carry 1 or 2 radicals $R^a$, which are selected from the group consisting of CN, $CH_3$, $OCH_3$, O-phenyl, O-naphthyl, S-phenyl, S-naphthyl, CI or F; and, if X is $C_1$-$C_4$-alkandiyl-C(O)—, the esters thereof, in particular the $C_1$-$C_4$-alkylesters thereof.

(I)

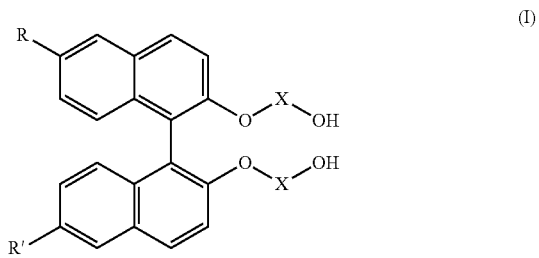

17 Claims, No Drawings

(56) References Cited

OTHER PUBLICATIONS

Patent Cooperation Treaty, International Searching Authority, Search Report and Written Opinion for PCT/EP2018/073245, 7 pages, dated Nov. 23, 2018.
Suzuki, A, et al., "Palladium-Catalyzed Cross-Coupling Reactions of Organoboron Compounds", Chem Rev 95, 2457-2483 (1995).
Yang, J, et al., "3-(4-Phenoxyphenyl)pyrazoles: A Novel Class of Sodium Channel Blockers", J Med Chem 47(6), 1547-1552 (2004).
Zhang, T, et al., "Pd-catalyzed Negishi coupling of pyrazole triflates with alkyl zinc halides", Tetrahedron Lett 52, 311-313 (2011).

BINAPHTHYL COMPOUNDS

CROSS-REFERENCE TO RELATED APPLICATION(S)

This application claims the benefit of priority of EP Application No. 17188576.7, filed Aug. 30, 2017.

The present invention relates to binaphthyl compounds, which are suitable as monomers for preparing polycarbonate resins having beneficial optical properties and which can be used for producing optical lenses.

Optical lenses made of optical resin instead of optical glass are advantageous in that they can be produced in large numbers by injection molding. Nowadays, optical resins, in particular, transparent polycarbonate resins, are frequently used for producing camera lenses. In this regard, resins with a higher refractive index are highly desirable, as they allow for reducing the size and weight of final products. In general, when using an optical material with a higher refractive index, a lens element of the same refractive power can be achieved with a surface having less curvature, so that the amount of aberration generated on this surface can be reduced. As a result, it is possible to reduce the number of lenses, to reduce the eccentric sensitivity of lenses and/or to reduce the lens thickness to thereby achieve weight reduction.

U.S. Pat. No. 9,360,593 describes polycarbonate resins having repeating units derived from binaphthyl monomers of the formula (A):

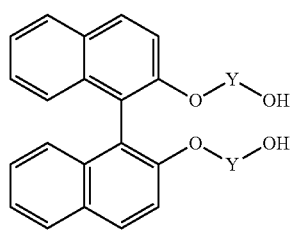

(A)

where Y is $C_1$-$C_4$-alkandiyl, in particular 1,2-ethandiyl. It is said that the polycarbonate resins have beneficial optical properties in terms of a high refractive index, a low Abbe's number, a high degree of transparency, low birefringence, and a glass transition temperature suitable for injection molding.

Co-Polycarbonates of monomers of the formula A with 10,10-bis(4-hydroxyphenyl)-anthrone monomers and their use for preparing optical lenses are described in US 2016/0319069.

Despite the advances made in the field of optical resins, there is still an ongoing need for monomers for preparing optical resins, in particular polycarbonate resins, which monomers result in a high refractive index, in particular which provide for a higher refractive index than the monomers of formula (A). Apart from that, the monomers should not impair the other optical properties of the optical resins, such as low Abbe's number, a high degree of transparency and low birefringence. Moreover, the monomers should be easy to prepare.

It was surprisingly found that compounds of the formula (I) as described herein are suitable for preparing optical resins of high transparency and high refractive index. In particular, when used as monomers in the preparation of optical resins, compounds of the formula (I) result in higher refractive indices than the monomers of formula (A).

Therefore, the present invention relates to compounds of the formula (I)

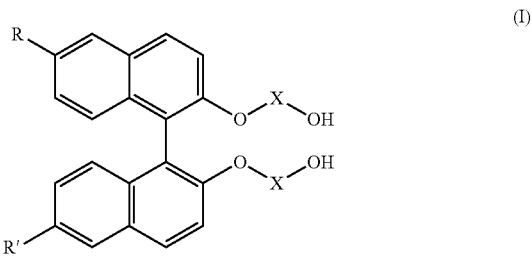

(I)

where
X is $C_2$-$C_4$-alkandiyl or $C_1$-$C_4$-alkandiyl-C(O)—, where C(O) is bound to the oxygen atom of the hydroxyl group and where $C_2$-$C_4$-alkandiyl or $C_1$-$C_4$-alkandiyl, respectively, are unsubstituted or carry a phenyl ring;
R and R' are identical or different and selected from mono- or polycyclic aryl having from 6 to 36 carbon atoms and mono- or polycyclic hetaryl having a total of 5 to 36 atoms, which are ring members, where 1, 2, 3 or 4 of these atoms are selected from nitrogen, sulfur and oxygen, while the remainder of these atoms are carbon atoms, where mono- or polycyclic aryl and mono- or polycyclic hetaryl are unsubstituted or carry 1 or 2 radicals $R^a$, which are selected from the group consisting of CN, $CH_3$, $OCH_3$, O-phenyl, O-naphthyl, S-phenyl, S-naphthyl and halogen, such as Cl or F,
and, if X is $C_1$-$C_4$-alkandiyl-C(O)—, the esters thereof, in particular the $C_1$-$C_4$-alkylesters thereof.

When used as monomers for the preparation of optical resins, in particular polycarbonate resins, the compounds of the formula (I) provide for higher refractive indices of the resins than the monomers of the formula (A). Moreover, compounds of formula (I) provide for high transparency of the resins and they do not significantly impair other optical properties. Apart from that, the monomers of formula (I) can be easily prepared and obtained in high yields and high purity. In particular, the compounds of formula (I) can be obtained in crystalline form, which allows for an efficient purification to the degree required in the preparation of optical resins. In particular, the compounds of formula (I) can be obtained in a purity which provides for low haze, which is in particular important for the use in the preparation of optical resins. Compounds of formula (I), which do not bear color-imparting radicals R, R' can also be obtained in a purity, which provides for a low yellowness index Y.I., as determined in accordance with ASTM E313, which may also be important for the use in the preparation of optical resins.

The compounds of formula (I) may have axial chirality due to the limited rotation along the bond between the naphthalene units and therefore compounds of the formula (I) may exist in the form of their (S)-enantiomers and their (R)-enantiomer. Consequently, the compounds of formula (I) may exist as a racemic mixture or as non-racemic mixtures or in the form of their pure (S)- and (R)-enantiomers, respectively. The present invention relates to both the racemic and the non-racemic mixtures of the enantiomers of the compounds of formula (I) and also to their pure (S)- and (R)-enantiomers.

In terms of the present invention, the terms "$C_1$-$C_4$-alkandiyl" refers to a bivalent, saturated, aliphatic hydrocarbon radical having 1, 2, 3 or 4 carbon atoms. Examples of $C_1$-$C_4$-alkandiyl are in particular 1,1-methandiyl ($C_1$-alkandiyl) and linear $C_2$-$C_4$-alkandiyl such as 1,2-ethandiyl (=$CH_2CH_2$), 1,3-propandiyl (=$CH_2CH_2CH_2$) and 1,4-butdandiyl(=$CH_2CH_2CH_2CH_2$), but also branched $C_2$-$C_4$-alkandiyl such as ethan-1,1-diyl, 1-methyl-1,2-ethandiyl, 1-methyl-1,2-propandiyl, 2-methyl-1,2-propandiyl, 2-methylpropan-1,3-diyl and 1,3-butandiyl. The term "$C_2$-$C_4$-alkandiyl" has the same meaning with the exception that 1,1-methandiyl is not included. Accordingly, examples of $C_2$-$C_4$-alkandiyl are in particular the linear alkandiyl radicals but also the branched alkandiyl radicals mentioned above.

In terms of the present invention, the term "halogen" refers to fluorine, chlorine, bromine or iodine radicals. In the context of $R^a$, the term "halogen" refers in particular to fluorine or chlorine.

In terms of the present invention, the term "monocyclic aryl" refers to phenyl.

In terms of the present invention, the terms "O-phenyl" and "O-naphthyl" refer to a phenyl or naphthyl radical which is attached to the remainder of the molecule via a oxygen atom. Likewise, the terms "S-phenyl" and "S-naphthyl" refer to a phenyl or naphthyl radical which is attached to the remainder of the molecule via a sulfur atom.

In terms of the present invention, the phrase "if X is $C_1$-$C_4$-alkandiyl-C(O)—, the esters thereof, in particular the $C_1$-$C_4$-alkylesters thereof" is understood that the hydroxyl group of X—OH together with the group C(O)— forms a carboxyl group which may be esterified with an alcohol, in particular with an aliphatic alcohol, more particularly with a $C_1$-$C_4$-alkanol such as methanol, ethanol, n-propanol, isopropanol, n-butanol, sec-butanol, isobutanol or tert.-butanol.

In terms of the present invention, the term "polycyclic aryl" refers to an aromatic polycyclic hydrocarbon radical, i.e. a completely unsaturated polycyclic hydrocarbon radical, where each of the carbon atoms is part of a conjugate π-electron system, indenyl, or a polycyclic hydrocarbon radical, which bears at least 2 phenyl rings, which are linked to each other by a covalent bond or which are fused to each other directly or which are fused to a saturated or unsaturated 4 to 10-membered mono- or bicyclic hydrocarbon ring. Usually polycylic aryl has from 9 to 36, e.g. 9, 10, 12, 13, 14, 16, 17, 18, 19, 20, 22, 24, 25, 26, 28, 30 or 35 carbon atoms, in particular from 10 to 20 carbon atoms, especially 10, 12, 13, 14 or 16 carbon atoms.

Polycylic aryl includes, by way of example 1H-indenyl, naphthyl, azulenyl, 9H-fluorenyl, phenanthryl, anthracenyl, pyrenyl, acenaphthenyl, acenaphthylenyl, cyclopent[fg]acenaphthylenyl, 2,3-dihydrophenalenyl, fluoranthenyl, benzo[k]fluoranthenyl, biphenylenyl, triphenylenyl, tetraphenylenyl, dibenzo[a,e][8]annulenyl, perylenyl, biphenyl, terphenyl, naphthylenphenyl, phenanthrylphenyl, anthracenylphenyl, pyrenylphenyl, 9H-fluorenylphenyl, di(naphthylen)phenyl, naphthylenbiphenyl, tri(phenyl)phenyl, tetra(phenyl)phenyl, pentaphenyl(phenyl), phenylnaphthyl, binaphthyl, phenanthrylnaphthyl, pyrenylnaphthyl, phenylanthracenyl, biphenylanthracenyl, naphthalenylanthracenyl, phenanthrylanthracenyl, dibenzo[a,e][8]annulenyl, 9,10-dihydro-9,10[1',2']benzoanthracenyl, 9,9'-spirobi-9H-fluorenyl and spiro[1H-cyclobuta-de]naphthalene-1,9'-[9H-fluoren]yl.

In terms of the present invention, the term "monocyclic hetaryl" refers to a heteroaromatic monocycle, where the ring member atoms are part of a conjugate π-electron system, where the heteroaromatic monocycle has 5 or 6 ring atoms, which comprise 1, 2, 3 or 4 nitrogen atoms or 1 oxygen atom and 0, 1, 2 or 3 nitrogen atoms or 1 sulfur atom and 0, 1, 2 or 3 nitrogen atoms, where the remainder of the ring atoms are carbon atoms. Examples include furyl, thienyl pyrrolyl, imidazolyl, pyrazolyl, 1,2,3-triazolyl, 1,2,4-triazolyl, tetrazolyl, oxazolyl, thiazolyl, isoxazolyl, isothiazolyl, 1,3,4-oxadiazolyl, 1,3,4-thiadiazolyl, pyridyl, pyrazinyl, pyridazinyl, pyrimidinyl and triazinyl.

In terms of the present invention, the term "polycyclic hetaryl" refers to heteroaromatic polycyclic radicals, which bear a monocyclic hetaryl ring as defined above and at least one, e.g. 1, 2, 3, 4 or 5, further aromatic rings selected from phenyl and heteroaromatic monocycles as defined above, where the aromatic rings of polycyclic hetaryl are linked to each other by a covalent bond or fused to each other directly and/or fused to a saturated or unsaturated 4 to 10-membered mono- or bicyclic hydrocarbon ring. The term "polycyclic hetaryl" also refers to heteroaromatic polycyclic radicals, which bear at least one saturated or partially unsaturated 5- or 6-membered heterocyclic ring bearing 1 or 2 heteroatoms selected from oxygen, sulfur and nitrogen as ring atoms, such as 2H-pyran, 4H-pyran, 1,4-dihydropyridin, 4H-1,4-oxazin, 4H-1,4-thiazin, 1,4-dioxin or 1,4-dithiin, and at least one, e.g. 1, 2, 3, 4 or 5, further aromatic rings selected from phenyl and heteroaromatic monocycles, where at least one of the further aromatic rings is directly fused to the saturated or partially unsaturated 5- or 6-membered heterocyclic radical and where the remainder of further aromatic rings of polycyclic hetaryl are linked to each other by a covalent bond or fused to each other directly and/or fused to a saturated or unsaturated 4 to 10-membered mono- or bicyclic hydrocarbon ring. Usually polycylic hetaryl has 9 to 36 ring atoms in particular 9 to 20 ring atoms, which comprise 1, 2, 3 or 4 nitrogen atoms or 1 oxygen atom and 0, 1, 2 or 3 nitrogen atoms, where the remainder of the ring atoms are carbon atoms.

Examples of polycyclic hetaryl include, but are not limited to, benzofuryl, benzothienyl, dibenzofuranyl, dibenzothienyl, naphthofuryl, naphthothienyl, furo[3,2-b]furanyl, thieno[3,2-b]thienyl, furo[2,3-b]furanyl, thieno[2,3-b]thienyl, furo[3,4-b]furanyl, thieno[3,4-b]thienyl, oxanthrenyl, thianthrenyl, indolyl, isoindolyl, carbazolyl, indolizinyl, benzopyrazolyl, benzimidazolyl, benzoxazolyl, benzothiazolyl, benzo[cd]indolyl, 1H-benzo[g]indolyl, quinolinyl, isoquinolinyl, acridinyl, phenazinyl, quinazolinyl, quinoxalinyl, phenoxazinyl, phenthiazinyl, benzo[b][1,5]naphthyridinyl, cinnolinyl, 1,5-naphthyridinyl, 1,8-naphthyridinyl, phenylpyrrolyl, naphthylpyrrolyl, dipyridyl, phenylpyridyl, naphthylpyridyl, pyrido[4,3-b]indolyl, pyrido[3,2-b]indolyl, pyrido[3,2-g]quinolinyl, pyrido[2,3-b][1,8]naphthyridinyl, pyrrolo[3,2-b]pyridinyl, pteridinyl, puryl, 9H-xanthenyl, 9H-thioxanthenyl, 2H-chromenyl, 2H-thiochromenyl, phenanthridinyl, phenanthrolinyl, furo[3,2-f][1]benzofuranyl, thieno[3,2-f][1]benzothienyl, furo[2,3-f][1]benzofuranyl, thieno[2,3-f][1]benzothienyl, furo[3,2-g]quinolinyl, thieno[3,2-g]quinolinyl, furo[2,3-g]quinolinyl, thieno[2,3-g]quinolinyl, furo[2,3-g]quinoxalinyl, thieno[2,3-g]quinoxalinyl, benzo[g]chromenyl, benzo[g]thiochromenyl, pyrrolo[3,2,1-h/']indolyl, benzo[g]quinoxalinyl, benzo[f]quinoxalinyl, and benzo[h]isoquinolinyl.

For the purpose of the invention, the radicals R and R' may be identical or different. Preferably, the radicals R and R' are identical, in particular for reasons of synthesis.

Preferably, the radicals R and R' are selected from mono- or polycyclic aryl having from 6 to 36 carbon atoms and mono- or polycyclic hetaryl having a total of 5 to 36 atoms, which are ring members, where 1, 2, 3 or 4 of these atoms are selected from nitrogen, sulfur and oxygen, while the remainder of these atoms are carbon atoms, where mono- or polycyclic aryl and mono- or polycyclic hetaryl are unsubstituted.

For the purpose of the invention, a particular group of embodiments relates to compounds of the formula (I), where the radicals R and R' are in particular selected from the group consisting of phenyl and polycyclic aryl as defined herein, where phenyl and polycyclic aryl are unsubstituted or substituted as defined herein and where phenyl and polycyclic aryl are in particular unsubstituted.

More preferably, the radicals R and R' are selected from the group consisting of:
- azulenyl, e.g. 1-azulenyl, 2-azulenyl, 3-azulenyl, 5-azulenyl or 6-azulenyl;
- indenyl, e.g. 1H-inden-1-yl, 1H-inden-2-yl, 1H-inden-3-yl, 1H-inden-4-yl, 1H-inden-5-yl, 1H-inden-6-yl or 1H-inden-6-yl, where indenyl is unsubstituted or substituted by 1, 2, 3, 4 or 5 radicals selected from phenyl and polycyclic aryl bearing 2, 3 or 4 phenyl rings, which are linked to each other via a single bond, directly fused to each other and/or fused to a saturated or unsaturated 4- to 10-membered mono- or bicyclic hydrocarbon ring, and where indenyl is in particular substituted or substituted by 1, 2 or 3 phenyl radicals;
- phenyl, which is unsubstituted;
- phenyl, which is substituted by 1 or 2 CN radicals;
- phenyl which is substituted by 1, 2, 3, 4 or 5 radicals selected from phenyl and polycyclic aryl bearing 2, 3 or 4 phenyl rings, which are linked to each other via a single bond, directly fused to each other and/or fused to a saturated or unsaturated 4- to 10-membered mono- or bicyclic hydrocarbon ring; and
- polycyclic aryl bearing 2, 3 or 4 phenyl rings, which are directly fused to each other, such as in naphthyl, anthracenyl, phenanthryl, pyrenyl or triphenylenyl, and/or fused to a saturated or unsaturated 4- to 10-membered mono- or bicyclic hydrocarbon ring, where polycyclic aryl is unsubstituted or substituted by 1 or 2 radicals selected from phenyl and polycyclic aryl bearing 2 or 3 phenyl rings, which are linked to each other via a single bond, directly fused to each other and/or fused to a saturated 4- to 10-membered mono- or bicyclic hydrocarbon ring, where the phenyl rings of polycyclic aryl are unsubstituted or carry 1 or 2 radicals $R^a$.

In this context, polycyclic aryl bearing 2, 3 or 4 phenyl rings which are linked to each other via a single bond include e.g. biphenyl and terphenyl. Polycyclic aryl bearing 2, 3 or 4 phenyl rings which are directly fused to each other include e.g. naphthyl, anthracenyl, phenanthryl, pyrenyl and triphenylenyl. Polycyclic aryl bearing 2, 3 or 4 phenyl rings which are fused to a saturated or unsaturated 4- to 10-membered mono- or bicyclic hydrocarbon ring include e.g. fluorenyl, biphenylenyl, tetraphenylenyl, acenaphtenyl, acenaphthylenyl, cyclopent[fg]acenaphthylenyl, phenalenyl, fluoranthenyl, benzo[k]fluoranthenyl, perylenyl, 9,10-dihydro-9,10[1',2']-benzenoanthracenyl, dibenzo[a,e][8]annulenyl, 9,9'-spirobi[9H-fluoren]yl and spiro[1H-cyclobutade]naphthalene-1,9'-[9H-fluoren]yl.

Examples of such preferred radicals include but are not limited to
phenyl, and substituted phenyl, such as: 2-cyanophenyl, 3-cyanophenyl, 4-cyanophenyl, biphenyl-4-yl, biphenyl-3-yl, biphenyl-2-yl, [1,1':4',1''-terphenyl]-4-yl, 4-(naphthalen-1-yl)phenyl, 3-(naphthalen-1-yl)phenyl, 2-(naphthalen-1-yl)phenyl, 4-(naphthalen-2-yl)phenyl, 3-(naphthalen-2-yl)phenyl, 2-(naphthalen-2-yl)phenyl, 4-(phenanthren-9-yl)phenyl, 4-(phenanthren-4-yl)phenyl, 4-(phenanthren-3-yl)phenyl, 4-(phenanthren-2-yl)phenyl, 4-(phenanthren-1-yl)phenyl, 3-(phenanthren-9-yl)phenyl, 3-(phenanthren-4-yl)phenyl, 3-(phenanthren-3-yl)phenyl, 3-(phenanthren-2-yl)phenyl, 3-(phenanthren-1-yl)phenyl, 2-(phenanthren-9-yl)phenyl, 4-(anthracen-9-yl)phenyl, 3-(anthracen-9-yl)phenyl, 4-(pyren-1-yl)phenyl, 4-(pyren-2-yl)phenyl, 4-(pyren-4-yl)phenyl, 3-(pyren-1-yl)phenyl, 3-(pyren-2-yl)phenyl, 3-(pyren-4-yl)phenyl, 4-(9H-fluoren-2-yl)phenyl, 3-(9H-fluoren-2-yl)phenyl, [1,1':3',1''-terphenyl]-5'-yl, 1,1':3',1''-terphenyl-5'-yl, [1,1':2',1''-terphenyl]-4'-yl, 3,5-di(1-naphthalenyl)phenyl, 3,5-di(2-naphthalenyl)phenyl, 5-(1-naphthalenyl)[1,1'-biphenyl]-3-yl, 5-(2-naphthalenyl)[1,1'-biphenyl]-3-yl, 3'-phenyl-1,1':2',1''-terphenyl, 3',4'-diphenyl-1,1':2',1''-terphenyl, and 4',5',6'-triphenyl-1,1':2',1''-terphenyl (pentaphenylphenyl);

naphthyl and substituted naphthyl, such as: 1-naphthyl, 2-naphthyl, 2-cyano-1-naphthyl, 3-cyano-1-naphthyl, 4-cyano-1-naphthyl, 5-cyano-1-naphthyl, 6-cyano-1-naphthyl, 7-cyano-1-naphthyl, 8-cyano-1-naphthyl, 1-cyano-2-naphthyl, 3-cyano-2-naphthyl, 4-cyano-2-naphthyl, 5-cyano-2-naphthyl, 6-cyano-2-naphthyl, 7-cyano-2-naphthyl, 8-cyano-2-naphthyl, 2-phenylnaphthalen-1-yl, 3-phenylnaphthalen-1-yl, 4-phenylnaphthalen-1-yl, 5-phenylnaphthalen-1-yl, 6-phenylnaphthalen-1-yl, 7-phenylnaphthalen-1-yl, 8-phenylnaphthalen-1-yl, 1-phenylnaphthalen-2-yl, 3-phenylnaphthalen-2-yl, 4-phenylnaphthalen-2-yl, 5-phenylnaphthalen-2-yl, 6-phenylnaphthalen-2-yl, 7-phenylnaphthalen-2-yl, 8-phenylnaphthalen-2-yl, 2-(naphthalen-1-yl)naphthalen-1-yl, 3-(naphthalen-1-yl)naphthalen-1-yl, 4-(naphthalen-1-yl)naphthalen-1-yl, 5-(naphthalen-1-yl)naphthalen-1-yl, 6-(naphthalen-1-yl)naphthalen-1-yl, 7-(naphthalen-1-yl)naphthalen-1-yl, 8-(naphthalen-1-yl)naphthalen-1-yl, 1-(naphthalen-1-yl)naphthalen-2-yl, 3-(naphthalen-1-yl)naphthalen-2-yl, 4-(naphthalen-1-yl)naphthalen-2-yl, 5-(naphthalen-1-yl)naphthalen-2-yl, 6-(naphthalen-1-yl)naphthalen-2-yl, 7-(naphthalen-1-yl)naphthalen-2-yl, 8-(naphthalen-1-yl)naphthalen-2-yl, 2-(naphthalen-2-yl)naphthalen-1-yl, 3-(naphthalen-2-yl)naphthalen-1-yl, 4-(naphthalen-2-yl)naphthalen-1-yl, 5-(naphthalen-2-yl)naphthalen-1-yl, 6-(naphthalen-2-yl)naphthalen-1-yl, 7-(naphthalen-2-yl)naphthalen-1-yl, 8-(naphthalen-2-yl)naphthalen-1-yl, 1-(naphthalen-2-yl)naphthalen-2-yl, 3-(naphthalen-2-yl)naphthalen-2-yl, 4-(naphthalen-2-yl)naphthalen-2-yl, 5-(naphthalen-2-yl)naphthalen-2-yl, 6-(naphthalen-2-yl)naphthalen-2-yl, 7-(naphthalen-2-yl)naphthalen-2-yl, 8-(naphthalen-2-yl)naphthalen-2-yl, 2-(phenanthren-9-yl)naphthalen-1-yl, 3-(phenanthren-9-yl)naphthalen-1-yl, 4-(phenanthren-9-yl)naphthalen-1-yl, 5-(phenanthren-9-yl)naphthalen-1-yl, 6-(phenanthren-9-yl)naphthalen-1-yl, 7-(phenanthren-9-yl)naphthalen-1-yl, 8-(phenanthren-9-yl)naphthalen-1-yl, 1-(phenanthren-9-yl)naphthalen-2-yl, 3-(phenanthren-9-yl)naphthalen-2-yl, 4-(phenanthren-9-yl)naphthalen-2-yl, 5-(phenanthren-9-yl)naphthalen-2-yl, 6-(phenanthren-9-yl)naphthalen-2-yl, 7-(phenanthren-9-yl)naphthalen-2-yl, 8-(phenanthren-9-yl)naphthalen-2-yl, 2-(phenanthren-4-yl)naphthalen-1-yl, 2-(phenanthren-3-yl)naphthalen-1-yl, 2-(phenanthren-2-yl)naphthalen-1-yl, 2-(phenanthren-1-yl)naphthalen-1-yl, 3-(phenanthren-4-yl)naphthalen-1-yl, 3-(phenanthren-3-yl)naphthalen-1-yl, 3-(phenanthren-2-yl)naphthalen-1-yl, 3-(phenanthren-1-yl)naphthalen-1-yl, 4-(phenanthren-4-yl)naphthalen-1-yl, 4-(phenanthren-3-yl)naphthalen-1-yl, 4-(phenanthren-2-yl)naphthalen-1-yl, 4-(phenanthren-1-yl)naphthalen-1-yl, 5-(phenanthren-4-yl)naphthalen-1-yl, 5-(phenanthren-3-yl)naphthalen-1-yl, 5-(phenanthren-2-yl)naphthalen-1-yl, 5-(phenanthren-1-yl)naphthalen-1-yl, 6-(phenanthren-4-yl)naphthalen-1-yl, 6-(phenanthren-3-yl)naphthalen-1-yl, 6-(phenanthren-2-yl)naphthalen-1-yl, 6-(phenanthren-1-yl)naphthalen-1-yl, 7-(phenanthren-4-yl)naphthalen-1-yl, 7-(phenanthren-3-yl)naphthalen-1-yl, 7-(phenanthren-2-yl)naphthalen-1-yl, 7-(phenanthren-1-yl)naphthalen-1-yl, 8-(phenanthren-4-yl)naphthalen-1-yl, 8-(phenanthren-3-yl)naphthalen-1-yl, 8-(phenanthren-2-yl)naphthalen-1-yl, 8-(phenanthren-1-yl)naphthalen-1-yl, 4-(pyren-1-yl)naphthalen-1-yl, 4-(pyren-2-yl)naphthalen-1-yl, 4-(pyren-4-yl)naphthalen-1-yl, 5-(pyren-1-yl)naphthalen-1-yl, 5-(pyren-2-yl)naphthalen-1-yl, 5-(pyren-4-yl)naphthalen-1-yl, 6-(pyren-1-yl)naphthalen-2-yl, 6-(pyren-2-yl)naphthalen-2-yl, and 6-(pyren-4-yl)naphthalen-2-yl;

azulenyl such as: 1-azulenyl, 2-azulenyl, 3-azulenyl, 5-azulenyl and 6-azulenyl;

indenyl, such as: 1H-inden-1-yl, 1H-inden-2-yl, 1H-inden-3-yl, 1H-inden-4-yl, 1H-inden-5-yl, 1H-inden-6-yl and 1H-inden-6-yl and indenyl, substituted by 1, 2 or 3 phenyl rings, such as 2-phenyl-1H-inden-1-yl, 2-phenyl-1H-inden-3-yl, 2-phenyl-1H-inden-4-yl, 2-phenyl-1H-inden-5-yl, 2-phenyl-1H-inden-6-yl, 3-phenyl-1H-inden-1-yl, 3-phenyl-1H-inden-2-yl, 3-phenyl-1H-inden-4-yl, 3-phenyl-1H-inden-5-yl, 3-phenyl-1H-inden-6-yl, 2,3-diphenyl-1H-inden-1-yl, 2,3-diphenyl-1H-inden-4-yl, 2,3-diphenyl-1H-inden-5-yl and 2,3-diphenyl-1H-inden-6-yl;

acenaphenyl, acenaphtylenyl and 2,3-dihydro-1H-phenalenyl, such as: acenaphthen-5-yl (1,2-dihydroacenaphthylen-5-yl), acenaphthen-4-yl (1,2-dihydroacenaphthylen-4-yl), acenaphthen-3-yl (1,2-dihydroacenaphthylen-3-yl), 5-acenaphthylenyl, 4-acenaphthylenyl, 3-acenaphthylenyl, 1-acenaphthylenyl, 2,3-dihydro-1H-phenalen-6-yl, 2,3-dihydro-1H-phenalen-5-yl and 2,3-dihydro-1H-phenalen-4-yl, fluoranthenyl and benzo[k]fluoranthenyl such as: 3-fluoranthenyl, 2-fluoranthenyl, 1-fluoranthenyl, benzo[k]fluoranthen-3-yl, benzo[k]fluoranthen-2-yl and benzo[k]fluoranthen-1-yl;

anthracenyl and substituted anthracenyl, such as: 1-anthryl (anthracen-1-yl), 2-anthryl (anthracen-2-yl), 9-anthryl (anthracen-9-yl), 10-phenylanthracen-9-yl, 10-[1,1'-biphenyl]-4-yl-9-anthracenyl, 10-[1,1'-biphenyl]-3-yl-9-anthracenyl, 10-(1-naphthalenyl)-9-anthracenyl, 10-(2-naphthalenyl)-9-anthracenyl and 10-(9-phenanthrenyl)-9-anthracenyl, 9H-fluorenyl, such as: 9H-fluoren-1-yl, 9H-fluoren-2-yl, 9H-fluoren-3-yl, 9H-fluoren-4-yl, and 9H-fluoren-9-yl, biphenylenyl such as: 1-biphenylenyl and 1-biphenylenyl;

phenanthryl, such as: 9-phenanthryl, 4-phenanthryl, 3-phenanthryl, 2-phenanthryl and 1-phenanthryl;

pyrenyl, such as: 1-pyrenyl, 2-pyrenyl and 4-pyrenyl;

triphenylenyl, such as 1-triphenylenyl and 2-triphenylenyl;

tetraphenylenyl, such as 1-tetraphenylenyl and 2-tetraphenylenyl;

perylenyl, such as: 3-perylenyl, 2-perylenyl and 2-perylenyl;

aryl bearing 4 phenyl rings fused to saturated 8 or 9-membered carbobicycles, such as: dibenzo[a,e][8]annulen-1-yl, dibenzo[a,e][8]annulen-2-yl, dibenzo[a,e][8]annulen-5-yl, 9,10-dihydro-9,10[1',2']-benzenoanthracen-2-yl, 9,10-dihydro-9,10[1',2']-benzeno-anthracen-1-yl, 9,9'-spirobi[9H-fluoren]-2-yl, 9,9'-spirobi[9H-fluoren]-3-yl, 9,9'-spirobi[9H-fluoren]-4-yl and spiro[1H-cyclobuta[de]naphthalene-1,9'-[9H]fluoren]-2'-yl.

In this group of embodiments, the radicals R and R' are in particular selected from the group consisting of:
phenyl, which is unsubstituted;
phenyl, which is substituted by 1, 2, 3, 4 or 5, in particular by 1, 2 or 3 phenyl radicals;
phenyl, which is substituted by 1 or 2 CN radicals, in particular by 1 CN radical;
phenyl, which is substituted by 1 or 2 polycyclic aryl radicals selected from biphenyl, naphthyl, fluorenyl, anthracenyl, phenanthryl and pyrenyl and optionally further substituted by 1 phenyl radical;
naphthyl, which is unsubstituted or substituted by 1 or 2 radicals selected from CN, phenyl and polycyclic aryl selected from biphenyl, naphthyl, fluorenyl, anthracenyl, phenanthryl and pyrenyl;
biphenylenyl;
triphenylenyl;
tetraphenylenyl;
phenanthryl;
pyrenyl;
9H-fluorenyl;
dibenzo[a,e][8]annulenyl;
perylenyl; and
9,9'-spirobi[9H-fluoren]yl.

More particularly, the radicals R and R' are selected from the group consisting of phenyl, naphthyl and phenanthrenyl. Especially, R and R' are selected from the group consisting of phenyl, 2-cyanophenyl, 3-cyanophenyl, 4-cyanophenyl, 2-naphthyl, 1-naphthyl, and 9-phenanthryl.

In another group of embodiments, at least one and in particular both of R and R' are selected from the group consisting of mono- or polycyclic hetaryl having a total of 5 to 36 atoms, in particular from the group consisting of:
monocyclic hetaryl, i.e. a heteroaromatic monocyclic radical, having 5 or 6 ring atoms, which comprise 1, 2, 3 or 4 nitrogen atoms or 1 oxygen atom and 0, 1, 2 or 3 nitrogen atoms or 1 sulfur atom and 0, 1, 2 or 3 nitrogen atoms, where the remainder of the ring atoms are carbon atoms,
heteroaromatic polycyclic radicals, which bear a heteroaromatic monocyclic ring as defined above and 1, 2, 3, 4 or 5, further aromatic rings selected from phenyl and heteroaromatic monocycles, where the aromatic rings of said heteroaromatic polycyclic radicals are linked to each other by a covalent bond or fused to each other directly and/or fused to a saturated or unsaturated 4 to 10-membered mono- or bicyclic hydrocarbon ring; and
heteroaromatic polycyclic radicals, which bear at least one saturated or partially unsaturated 5- or 6-membered heterocyclic ring bearing 1 or 2 heteroatoms selected from oxygen, sulfur and nitrogen as ring atoms, such as 2H-pyran, 4H-pyran, 1,4-dihydropyridin, 4H-1,4-oxazin or 1,4-dioxin, and 1, 2, 3, 4 or 5 further aromatic rings selected from phenyl and heteroaromatic monocycles as defined above, where at least one of the further aromatic rings is directly fused to the saturated or partially unsaturated 5- or 6-membered heteroaromatic monocycle and where the remainder of further aromatic rings of polycyclic hetaryl are linked to each other by a covalent bond or fused to each other directly and/or fused to a saturated or unsaturated 4 to 10-membered mono- or bicyclic hydrocarbon ring.

In this other group of embodiments, at least one and in particular both of R and R' are in particular selected from the group consisting of mono- or polycyclic hetaryl, which is selected from the group consisting of:

monocyclic hetaryl, i.e. a heteroaromatic monocyclic radical, having 5- or 6 ring atoms, which comprise 1 or 2 nitrogen atoms or 1 sulfur atom or 1 oxygen atom and where the remainder of the ring atoms are carbon atoms, heteroaromatic polycyclic radicals, which bear a heteroaromatic monocyclic ring having 5 or 6 ring atoms which comprise 1 or 2 nitrogen atoms or 1 oxygen atom or 1 sulfur atom and where the remainder of the ring atoms are carbon atoms, and 1 or 2 further phenyl rings which are fused to the heteroaromatic monocyclic ring.

In this other group of embodiments, at least one and in particular both of R and R' are in particular selected from the group consisting of: furyl, thienyl, pyrrolyl, imidazolyl, pyrazolyl, 1,2,3-triazolyl, 1,2,4-triazolyl, tetrazolyl, oxazolyl, isoxazolyl, 1,3,4-oxadiazolyl, pyridyl, pyrazinyl, pyridazinyl, pyrimidinyl and triazinyl, benzofuryl, dibenzofuranyl, benzothienyl, dibenzothienyl, thianthrenyl, naphthofuryl, furo[3,2-b]furanyl, furo[2,3-b]furanyl, furo[3,4-b]furanyl, oxanthrenyl, indolyl, isoindolyl, carbazolyl, indolizinyl, benzopyrazolyl, benzimidazolyl, benzoxazolyl, benzo[cd]indolyl, 1H-benzo[g]indolyl, quinolinyl, isoquinolinyl, acridinyl, phenazinyl, quinazolinyl, quinoxalinyl, phenoxazinyl, benzo[b][1,5]naphthyridinyl, cinnolinyl, 1,5-naphthyridinyl, 1,8-naphthyridinyl, phenylpyrrolyl, naphthylpyrrolyl, dipyridyl, phenylpyridyl, naphthylpyridyl, pyrido[4,3-b]indolyl, pyrido[3,2-b]indolyl, pyrido[3,2-g]quinolinyl, pyrido[2,3-b][1,8]naphthyridinyl, pyrrolo[3,2-b]pyridinyl, pteridinyl, puryl, 9H-xanthenyl, 2H-chromenyl, phenanthridinyl, phenanthrolinyl, furo[3,2-f][1]benzofuranyl, furo[2,3-f][1]benzofuranyl, furo[3,2-g]quinolinyl, furo[2,3-g]quinolinyl, furo[2,3-g]quinoxalinyl, benzo[g]chromenyl, pyrrolo[3,2,1-hi]indolyl, benzo[g]quinoxalinyl, benzo[f]quinoxalinyl, and benzo[h]isoquinolinyl, with particular preference given to furyl, thienyl, pyrrolyl, imidazolyl, pyrazolyl, oxazolyl, isoxazolyl, pyridyl, pyrazinyl, pyridazinyl, pyrimidinyl benzofuryl, dibenzofuranyl, benzothienyl and dibenzothienyl.

In particular, at least one and in particular both of R and R' are in particular selected from the group consisting of:
  phenyl, which is unsubstituted;
  phenyl, which is substituted by 1, 2, 3, 4 or 5, in particular by 1, 2 or 3 phenyl radicals;
  phenyl, which is substituted by 1 or 2 CN radicals, in particular by 1 CN radical;
  phenyl, which is substituted by 1 or 2 polycyclic aryl radicals selected from biphenyl, naphthyl, fluorenyl, anthracenyl, phenanthryl and pyrenyl and optionally further substituted by 1 phenyl radical;
  naphthyl, which is unsubstituted or substituted by 1 or 2 radicals selected from CN, phenyl and polycyclic aryl selected from biphenyl, naphthyl, fluorenyl, anthracenyl, phenanthryl and pyrenyl;
  biphenylenyl;
  triphenylenyl;
  tetraphenylenyl;
  phenanthryl;
  pyrenyl;
  9H-fluorenyl;
  dibenzo[a,e][8]annulenyl;
  perylenyl; and
  9,9'-spirobi[9H-fluoren]yl.
  monocyclic hetaryl, i.e. a heteroaromatic monocyclic radical, having 5- or 6 ring atoms, which comprise 1 or 2 nitrogen atoms or 1 sulfur atom or 1 oxygen atom and where the remainder of the ring atoms are carbon atoms, heteroaromatic polycyclic radicals, which bear a heteroaromatic monocyclic ring having 5 or 6 ring atoms which comprise 1 or 2 nitrogen atoms or 1 oxygen atom or 1 sulfur atom and where the remainder of the ring atoms are carbon atoms, and 1 or 2 further phenyl rings which are fused to the heteroaromatic monocyclic ring.

More particularly, the radicals R and R' are selected from the group consisting of phenyl, which is unsubstituted or substituted by CN, naphthyl, phenanthrenyl, furyl, thienyl, pyrrolyl, imidazolyl, pyrazolyl, oxazolyl, isoxazolyl, pyridyl, pyrazinyl, pyridazinyl, pyrimidinyl benzofuryl, dibenzofuranyl, benzothienyl and dibenzothienyl. Especially, R and R' are selected from the group consisting of phenyl, 2-cyanophenyl, 3-cyanophenyl, 4-cyanophenyl, 2-naphthyl, 1-naphthyl, 9-phenanthryl dibenzo[b,d]thien-4-yl and dibenzo[b,d]furan-4-yl.

For the purpose of the invention, the radicals $R^a$, if present, are preferably selected from CN, $CH_3$ and F, and in particular are CN.

In particular, the compounds of formula (I) do not contain a radical $R^a$.

For the purpose of the invention, the radicals X in formula (I) are preferably $C_2$-$C_4$-alkandiyl and in particular 1,2-ethandiyl. Compounds, where X in formula (I) is 1,2-ethandiyl are also termed compounds of formula (Ia).

In another group of embodiments, the radicals X in formula (I) are $C_1$-$C_4$-alkandiyl-C(O)— and in particular $CH_2$—C(O)—.

Particular preference is given to the following compounds:

6,6'-diphenyl-2,2'-bis-(2-hydroxyethoxy)-1,1'-binaphthyl (compound of formula (Ia.1), 6,6'-di-(1-naphthyl)-2,2'-bis-(2-hydroxyethoxy)-1,1'-binaphthyl (compound of formula (Ia.2), 6,6'-di-(2-naphthyl)-2,2'-bis-(2-hydroxyethoxy)-1,1'-binaphthyl (compound of formula (Ia.3), 6,6'-di-(9-phenanthryl)-2,2'-bis-(2-hydroxyethoxy)-1,1'-binaphthyl (compound of formula (Ia.4), 6,6'-di-(3-cyanophenyl)-2,2'-bis-(2-hydroxyethoxy)-1,1'-binaphthyl (compound of formula (Ia.5), 6,6'-di-(dibenzo[b,d]furan-4-yl)-2,2'-bis-(2-hydroxyethoxy)-1,1'-binaphthyl (compound of formula (Ia.6) and 6,6'-di-(dibenzo[b,d]thien-4-yl)-2,2'-bis-(2-hydroxyethoxy)-1,1'-binaphthyl (compound of formula (Ia.7).

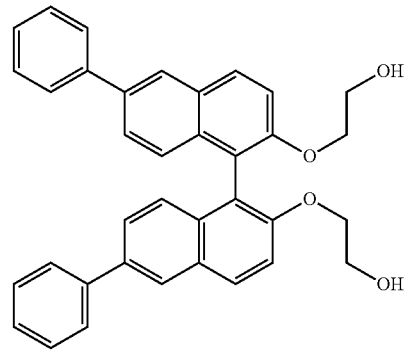

(Ia.1)

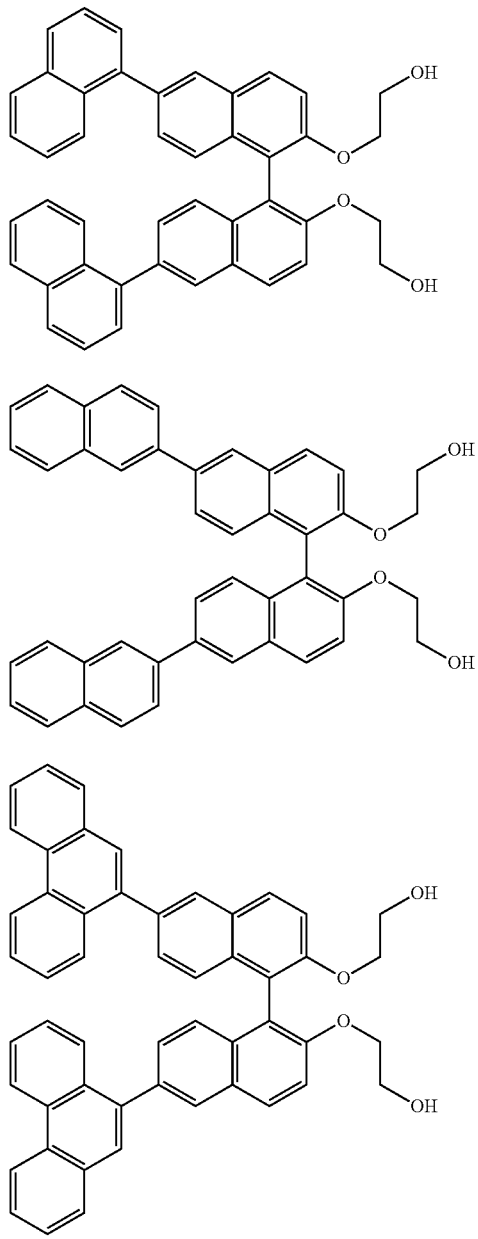

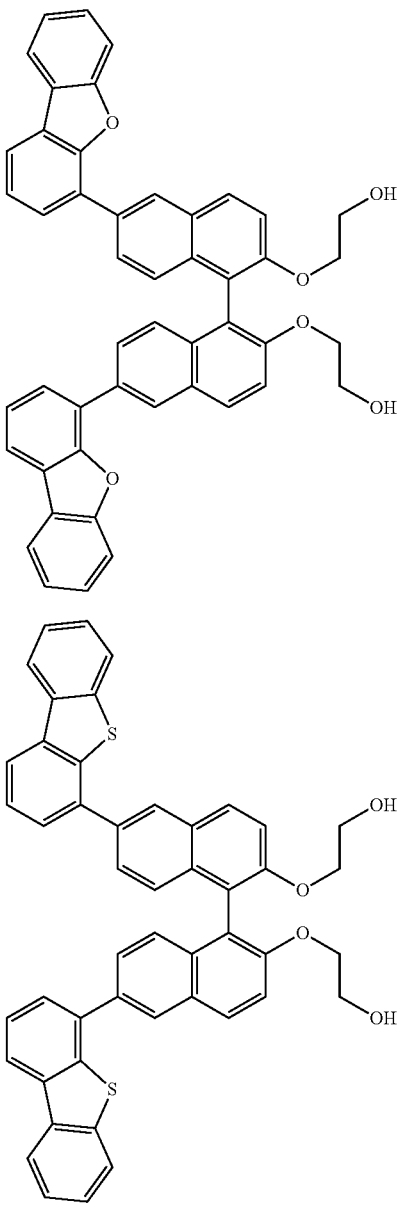

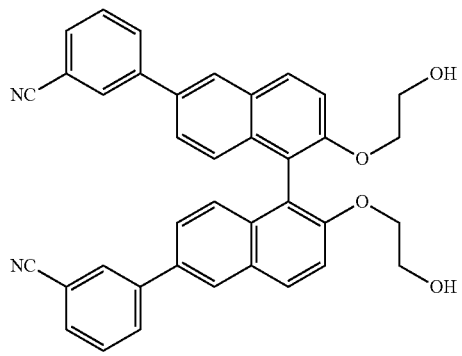

Particular preference is also given to the following compounds:

2,2'-{(6,6'-diphenyl[1,1'-binaphthalene]-2,2'-diyl)bis(oxy)}diacetic acid (compound of formula (Ib.1), 2,2'-{(6,6'-bis(1-naphthyl)phenyl[1,1'-binaphthalene]-2,2'-diyl)bis(oxy)}diacetic acid (compound of formula (Ib.2), 2,2'-{(6,6'-bis(2-naphthyl)phenyl[1,1'-binaphthalene]-2,2'-diyl)bis(oxy)}diacetic acid (compound of formula (Ib.3), 2,2'-{(6,6'-bis(9-phenanthryl)phenyl[1,1'-binaphthalene]-2,2'-diyl)bis(oxy)}diacetic acid (compound of formula (Ib.4), 2,2'-{(6,6'-bis(3-cyanophenyl)phenyl[1,1'-binaphthalene]-2,2'-diyl)bis(oxy)}diacetic acid (compound of formula (Ib.5), 2,2'-{(6,6'-bis(dibenzo[b,d]furan-4-yl)phenyl[1,1'-binaphthalene]-2,2'-diyl)bis(oxy)}diacetic acid (compound of formula (Ib.6), 2,2'-{(6,6'-bis(dibenzo[b,d]thien-4-yl)phenyl[1,1'-binaphthalene]-2,2'-diyl)bis(oxy)}diacetic acid (compound of formula (Ib.7), the corresponding methyl esters (compounds Ic.1 to Ic.7) and the corresponding ethyl esters (compounds Id.1 to Id.7), as structurally described in the following table A:

TABLE A

| Compound | Formula | R | R' | R" |
|---|---|---|---|---|
| Ib.1 | Ib | phenyl | phenyl | H |
| Ib.2 | Ib | 1-naphthyl | 1-naphthyl | H |
| Ib.3 | Ib | 1-naphthyl | 1-naphthyl | H |
| Ib.4 | Ib | 9-phenanthryl | 9-phenanthryl | H |
| Ib.5 | Ib | 3-cyanophenyl | 3-cyanophenyl | H |
| Ib.6 | Ib | dibenzo[b,d]furan-4-yl | dibenzo[b,d]furan-4-yl | H |
| Ib.7 | Ib | dibenzo[b,d]thien-4-yl | dibenzo[b,d]thien-4-yl | H |
| Ic.1 | Ic | phenyl | phenyl | $CH_3$ |
| Ic.2 | Ic | 1-naphthyl | 1-naphthyl | $CH_3$ |
| Ic.3 | Ic | 1-naphthyl | 1-naphthyl | $CH_3$ |
| Ic.4 | Ic | 9-phenanthryl | 9-phenanthryl | $CH_3$ |
| Ic.5 | Ic | 3-cyanophenyl | 3-cyanophenyl | $CH_3$ |
| Ic.6 | Ic | dibenzo[b,d]furan-4-yl | dibenzo[b,d]furan-4-yl | $CH_3$ |
| Ic.7 | Ic | dibenzo[b,d]thien-4-yl | dibenzo[b,d]thien-4-yl | $CH_3$ |
| Id.1 | Id | phenyl | phenyl | $C_2H_5$ |
| Id.2 | Id | 1-naphthyl | 1-naphthyl | $C_2H_5$ |
| Id.3 | Id | 1-naphthyl | 1-naphthyl | $C_2H_5$ |
| Id.4 | Id | 9-phenanthryl | 9-phenanthryl | $C_2H_5$ |
| Id.5 | Id | 3-cyanophenyl | 3-cyanophenyl | $C_2H_5$ |
| Id.6 | Id | dibenzo[b,d]furan-4-yl | dibenzo[b,d]furan-4-yl | $C_2H_5$ |
| Id.7 | Id | dibenzo[b,d]thien-4-yl | dibenzo[b,d]thien-4-yl | $C_2H_5$ |

Ib: R" = H, Ic: R" = $CH_3$; Id: R" = $C_2H_5$.

As stated above, the compounds of the present invention can be obtained in high purity, which means that a product is obtained, which does not contain significant amounts of organic impurities different from the compound of formula (I), except for volatiles. Usually, the purity of compounds of formula (I) is at least 95%, in particular at least 98% and especially at least 99%, based on the non-volatile organic matter, i.e. the product contains at most 5%, in particular at most 2% and especially at most 1% of non-volatile impurities different from the compound of formula (I).

The term "volatiles" refers to organic compounds, which have a boiling point of less than 200° C. at standard pressure (105 Pa). Consequently, non-volatile organic matter is understood to mean compounds having a boiling point, which exceeds 200° C. at standard pressure.

It is a particular benefit of the invention that the compounds of formula (I) can be obtained in crystalline form. In the crystalline form the compound of formula (I) may be present in pure form or in the form of a solvate with water or an organic solvent. Therefore, a particular aspect of the invention relates to the compounds of formula (I), which are essentially present in crystalline form. In particular, the invention relates to crystalline forms, where the compound of formula (I) is present without solvent and to the crystalline solvates of the compounds of formula (I), where the crystals contain a solvent incorporated.

It is a particular benefit of the invention that the compounds of the formula (I) and their solvates can be easily crystallized from conventional organic solvents. This allows for an efficient purification of the compounds of formula (I). Suitable organic solvents for crystallizing the compounds of the formula (I) or their solvates, include but are not limited to aromatic hydrocarbons such as toluene or xylene, aliphatic ketones in particular ketones having from 3 to 6 carbon atoms, such as acetone, methyl ethyl ketone, methyl isopropyl ketone or diethyl ketone, alicyclic ethers, such as dioxane or tetrahydrofurane, and aliphatic alcohols having 1 to 4 carbon atoms, such as methanol, ethanol or isopropanol, as well as mixtures thereof.

The compounds of the formula (I), where R and R' are identical and X is $C_2$-$C_4$-alkandiyl, can be prepared from readily available 1,1'-binaphthol (compound II) by the process according to the following reaction scheme 1a:

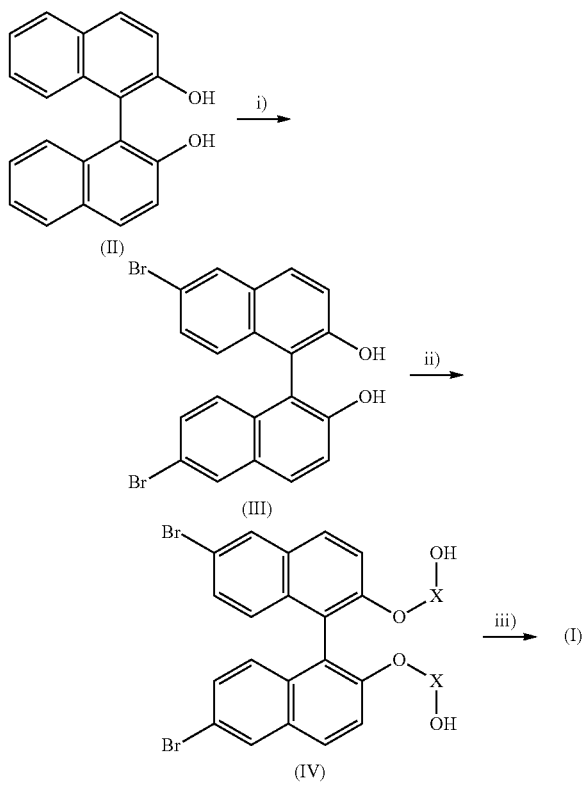

Scheme 1a

In step i) of the process according to scheme 1a, 1,1'-binaphthol is brominated to selectively yield the 6,6'-dibromo-1,1'-binaphthol of formula (III). Bromination can be simply achieved by mixing 1,1'-binaphthol at low temperatures with a suitable brominating reagent in a polar aprotic solvent, which is inert against bromination. Suitable brominating agents are in particular elemental bromine. Suitable polar aprotic solvents for step i) include aliphatic halogenated hydrocarbon compounds, such as dichloromethane, trichloromethane, dichloroethane or dibromomethane, esters, such as isopropyl acetate or ethyl acetate, and mixtures thereof. Suitable reaction temperatures for bromination of 1,1'-binaphthol with bromine are typically in the range from –100 to 10° C., in particular in the range from –100 to –30° C. or, alternatively, in the range from –10 to 10° C. Further details can be taken from Bunzen et al. J. Am. Chem. Soc., 2009, 131(10), 3621-3630. As an alternative, N-bromosuccinimide can be used as a bromination agent. In this case, reaction temperatures will be higher than for the bromination with elemental bromine, e.g. from 0 to 50° C. Suitable solvents may then, in addition to aliphatic halogenated hydrocarbons, also include aliphatic ketones having from 3 to 6 carbon atoms, such as acetone, methyl ethyl ketone, methyl isobutyl ketone or diethyl ketone, cyclic ethers having from 4 to 6 carbon atoms, such as tetrahydrofuran, dioxan, diethyl ether, cyclopentyl methyl ether, and other solvents like acetonitrile, dimethylformamide, chloroform, methylene chloride, dichloroethane, as well as mixtures thereof with aliphatic halogenated hydrocarbons.

As a further alternative 6,6'-dibromo-1,1'-binaphthol of formula (III) can also be synthesized by copper(II)-catalyzed oxidative coupling of 6-bromo-2-naphthol, e.g. in accordance with the procedure described in H. Egami et al., J. Am. Chem. Soc. 2009, 13 (17), 6082-83.

According to step ii) of scheme 1a the compound of formula (III) is reacted with a cyclic carbonate of the formula (V)

(V)

where X is as defined above and in particular 1,2-ethandiyl to yield the compound of formula (IV). Hence, an example of a suitable compound of formula (V) is ethylene carbonate. The compound of formula (V) is usually applied in excess of the desired stoichiometry, i.e. the molar ratio of compound (V) to the compound (Ill) exceeds 2:1 and is in particular in the range from 2.2:1 to 5:1. The reaction according to step ii) of scheme 1a is usually performed in the presence of a base, in particular an oxo base, especially an alkaline carbonate such as sodium carbonate or potassium carbonate. The base is usually used in catalytic amounts, e.g. in amount from 0.1 to 0.5 mol per 1 mol of the compound (Ill). Frequently, the reaction of the compound of formula (III) with the compound of formula (VI) is performed in an aprotic organic solvent, in particular in an aromatic hydrocarbon solvent such as toluene, xylene or anisole and mixtures thereof. The reaction according to step ii) of scheme 1a is usually performed at temperatures in the range from 50 to 150° C.

According to step iii) of scheme 1a the compound of formula (IV) is reacted with an arylboronic compound of the formula (VI)

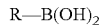

(VI)

where R is as defined for formula (I), or with an ester or anhydride of (VI), in particular a $C_1$-$C_4$-alkyl ester of (VI), in the presence of a transition metal catalyst, in particular in the presence of a palladium catalyst. Frequently, step iii) is performed under the conditions of a so-called "Suzuki Reaction" or "Suzuki Coupling" (see e.g. A. Suzuki et al., Chem. Rev. 1995, 95, 2457-2483; N. Zhe et al., J. Med. Chem. 2005, 48 (5), 1569-1609; Young et al., J. Med. Chem. 2004, 47 (6), 1547-1552; C. Slee et al., Bioorg. Med. Chem. Lett. 2001, 9, 3243-3253; T. Zhang et al., Tetrahedron Lett., 52 (2011), 311-313, S. Bourrain et al., Synlett. 5 (2004), 795-798, B. Li et al., Europ. J. Org. Chem. 2011 3932-3937). Suitable transition metal catalysts are in particular palladium compounds, which bear at least one palladium atom and at least one tri-substituted phosphine ligand. Examples of palladium catalysts are tetrakis(triphenylphosphine) palladium, tetrakis(tritolylphosphine) palladium and [1,1-bis(diphenylphosphino)ferrocene]dichloropalladium(II) ($PdCl_2$(dppf)). Frequently, the palladium catalysts are prepared in situ from a suitable palladium precursor and a suitable phosphine ligand. Suitable palladium precursors are palladium compounds such as tris-(dibenzylideneacetone)dipalladium(0) ($Pd_2(dba)_3$) or palladium(II) acetate ($Pd(OAc)_2$). Suitable phosphine ligands are in particular tri(substituted) phosphines, e.g. a triarylphosphines such as triphenylphosphine, tritolylphosphine or 2,2'-bis(diphenyl-phosphino)-1,1'-binaphthalene (BINAP), tri(cyclo)alkylphosphine such as tris-n-butylphosphine, tris(tert-butyl)phosphine or tris(cyclohexylphosphine), or dicyclohexyl-(2',4',6'-tri-iso-propyl-biphenyl-2-yl)-phosphane (X-Phos). Usually, the reaction is performed in the presence of a base, in particular an oxo base, such as an alkaline alkoxide, earth alkaline alkoxide, alkaline hydroxides, earth alkaline hydroxides, alkaline carbonate or earth alkaline carbonate such as or sodium ethoxide, sodium tert-butoxide, potassium tert-butoxide, lithium hydroxide, barium hydroxide, sodium carbonate, potassium carbonate, or cesium carbonate. Frequently, the reaction according to step iii) of scheme 1a is performed in an organic solvent or in a mixture thereof with water. If the reaction is performed in a mixture of an organic solvent and water, the reaction mixture may be monophasic or biphasic. Suitable organic solvents include but are not limited to aromatic hydrocarbons such as toluene or xylene, acyclic and cyclic ethers, such as methyl tert.-butyl ether, ethyl tert.-butyl ether, diisopropylether, dioxane or tetrahydrofurane, and aliphatic alcohols having 1 to 4 carbon atoms, such as methanol, ethanol or isopropanol, as well as mixtures thereof. The reaction according to step iii) of scheme 1a is usually performed at temperatures in the range from 50 to 150° C.

The sequence of steps i), ii) and iii) can be changed as depicted in the following schemes 1b and 1c.

Scheme 1b

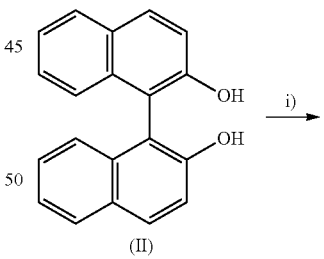

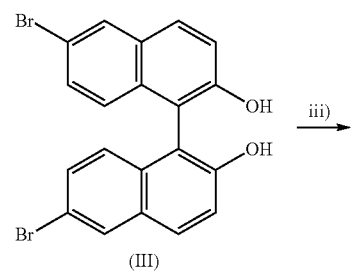

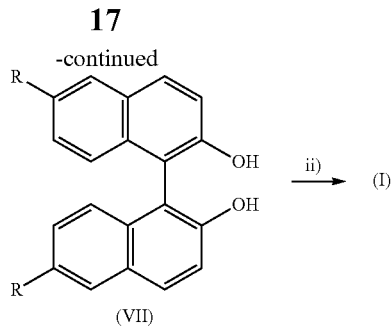

(VII)

Scheme 1c

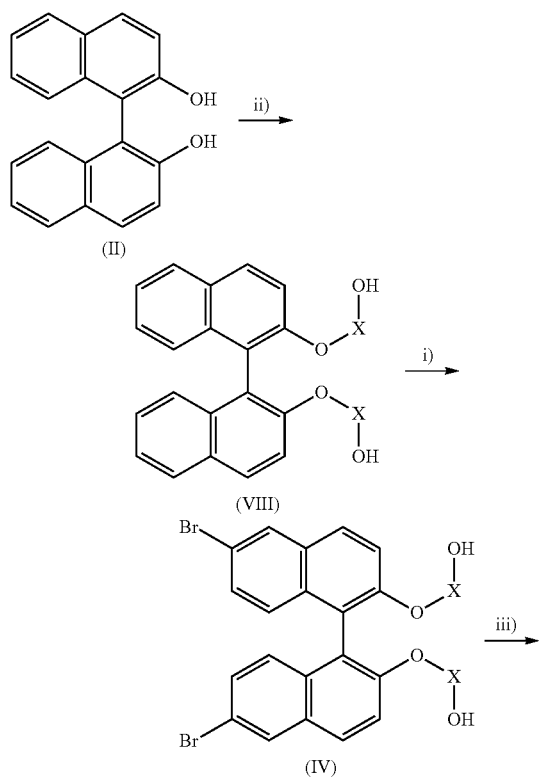

The reaction conditions in steps i), ii) and iii) of the processes according to schemes 1b and 1c are the same or almost the same as described for steps i), ii) and iii) of the process according to scheme 1a.

The compounds of the formula (I), where R and R' are identical and X—OH is $C_1$-$C_4$-alkandiyl-C(O)—OH, in particular —$CH_2$—C(O)—OH, or the alkyl ester thereof, i.e. $C_1$-$C_4$-alkandiyl-C(O)—O—$C_1$-$C_4$-alkyl, in particular —$CH_2$—C(O)—O—$C_1$-$C_4$-alkyl, can be prepared from the substituted binaphthol compound of formula (VII) by initially reacting it with a compound Hal-$C_1$-$C_4$-alkandiyl-C(O)O—$C_1$-$C_4$-alkyl, where Hal is bromine or chlorine and $C_1$-$C_4$-alkandiyl is in particular methylene. The reaction is carried out in the presence of a base, such as e.g. potassium carbonate, as described e.g. in T. Ema J. Org. Chem. 2010, 75(13), 4492-4500. If desired, the thus introduced groups $C_1$-$C_4$-alkandiyl-C(O)O—$C_1$-$C_4$-alkyl can afterwards be converted into groups $C_1$-$C_4$-alkandiyl-C(O)OH using well known procedures of ester hydrolysis. Alternatively, the compounds of the formula (I), where R and R' are identical and X—OH is $C_1$-$C_4$-alkandiyl-C(O)—OH or the alkyl ester thereof, can also be prepared by reacting the binaphthol (II) with Hal-$C_1$-$C_4$-alkandiyl-C(O)O—$C_1$-$C_4$-alkyl in the presence of a base as described above and subjecting the product obtained this way to the aforementioned reaction steps i) and iii). If a compound (1) with the moieties X—OH being $C_1$-$C_4$-alkandiyl-C(O)—OH instead of the alkyl esters thereof are desired, the ester groups are hydrolyzed by well-known methods preferably in a final step of the reaction sequence.

The reaction mixtures obtained in the individual steps i) to iii) of schemes 1a) to 1c) as well as the other reaction steps described above are worked up in a conventional way, e.g. by mixing with water, separating the phases and, where appropriate, purifying the crude products by chromatography or crystallization. The intermediates in some cases result in the form of colourless or pale brownish, viscous oils, which are freed of volatiles or purified under reduced pressure and at moderately elevated temperature. If the intermediates are obtained as solids, the purification can be achieved by recrystallization.

It is apparent to a skilled person that compounds, where R and R' are different, can be obtained by analogy to the methods depicted in schemes 1a) to 1c), e.g. by using mixtures of arylboronic compounds (VI) having different aryl radicals or by applying a step-wise reaction of the dibromo compounds of formulae (Ill) or (IV) with two different arylboronic compounds of formula (VI). By these methods, usually mixtures of compounds of the formula (I) will be obtained, which contain compounds of formula (I), where R and R' are identical and compounds of formula (I), where R and R' are different. These mixtures can be separated, e.g. by chromatography, to obtain the individual compounds of formula (I). For the purpose of the invention, i.e. the use of the compounds of formula (I) as monomers in the preparation of optical resins, it may not be necessary to resolve these mixtures. Rather, the mixtures may also be used as monomers.

Compounds, where R and R' are different can also be obtained by processes similar to the processes according to schemes 1a), 1b) and 1c), where in step i) the compounds of formulae (II) and (VIII), respectively, are subjected to monobromination instead of a dibromination, followed by steps iii) and optionally ii) to yield a compound having only one aromatic radical R. Then, a second bromination step i) is performed followed by a further step iii) using a different arylboronic compound R'—B(OH)$_2$ to yield a compound of formula (I) bearing two different aromatic radicals R and R'.

As mentioned above, the polycarbonate resins comprising monomers of the formula (I) in polymerized form provide high transparency and high refractive index to thermoplastic resins, which therefore are suitable for preparing optical devices, such as camera lenses, where high transparency and high refractive index is required. More precisely, the thermoplastic polycarbonates prepared from monomers of formula (I) are characterized by having a high refractive index, which is preferably at least 1.65, more preferably at least 1.70, in particular at least 1.75.

The contribution of the monomer of the formula (I) to the refractive index of the thermoplastic resin, in particular a polycarbonate resin, will depend from the refractive index of said monomer and the relative amount of said monomer in the thermoplastic resin. In general, a higher refractive index of the monomer contained in the thermoplastic resin will result in a higher refractive index of the resulting thermoplastic resin. Apart from that, the refractive index of a thermoplastic resin comprising monomers of formula (I) in polymerized form can be calculated from the refractive indices of the monomers used for preparing the thermoplastic resin or, alternatively, ab initio, e.g. by using the computer software ACD/ChemSketch 2012 (Advanced Chemistry Development, Inc.).

In case of thermoplastic copolymer resins, the refractive index of the thermoplastic resin, in particular a polycarbonate resin, can be calculated from the refractive indices of the homopolymers of the respective monomers, which form the copolymer resin, by the following so called "Fox equation":

$$1/n_D = x_1/n_{D1} + x_2/n_{D2} + \ldots x_n/n_{Dn},$$

where no is the refractive index of the copolymer, $x_1$, $x_2$, ... $x_n$ are the mass fractions of the monomers 1, 2, ... n in the copolymer and $n_{D1}$, $n_{D2}$, ... $n_{Dn}$ are the refractive indices of the homopolymers synthesized from only one of the monomers 1, 2, ... n at a time. In case of polycarbonates, $x_1$, $x_2$, ... $x_n$ are the mass fractions of the OH monomers 1, 2, ... n, based on the total amount of OH monomer. It is apparent that a higher refractive index of a homopolymer will result in a higher refractive index of the copolymer.

In the following table 1, the refractive indices $n_D$ of the homopolycarbonates of several compounds of the formula (I) at wavelength of 589 nm are summarized. The refractive indices of the homopolycarbonates of the compounds of formula (I) were determined indirectly. For this, co-polycarbonates of the respective monomer of formula (I) with 9,9-bis(4-(2-hydroxyethoxy)phenyl)fluorine and diphenyl carbonate were prepared according to the protocol of example 1 in column 48 of U.S. Pat. No. 9,360,593 and the refractive indices no of the co-polycarbonates were measured at wavelength of 589 nm in accordance with the protocol JIS-K-7142 using an Abbe refractometer and applying a 0.1 mm film of the co-polycarbonate. From the thus measured refractive indices no, the refractive index of the homopolycarbonate of the respective monomer was calculated by applying the Fox equation and the known refractive index of 9,9-bis(4-(2-hydroxyethoxy)phenyl)fluorine ($n_D$ (589 nm)=1.639).

TABLE 1

Refractive index $n_D$ of the homopolycarbonate at wavelength of 589 nm

| Compound | $n_D$ [1] |
|---|---|
| 2,2'-bis-(2-hydroxyethoxy)-1,1'-binaphthyl [2] | 1.668 |
| 6,6'-diphenyl-2,2'-bis-(2-hydroxyethoxy)-1,1'-binaphthyl (compound Ia. 1) | 1.697 |
| 6,6'-di-(1-naphthyl)-2,2'-bis-(2-hydroxyethoxy)-1,1'-binaphthyl (compound Ia. 2) | 1.716 |
| 6,6'-di-(2-naphthyl)-2,2'-bis-(2-hydroxyethoxy)-1,1'-binaphthyl (compound Ia. 3) | 1.742 |
| 6,6'-di-(9-phenanthryl)-2,2'-bis-(2-hydroxyethoxy)-1,1'-binaphthyl (compound Ia. 4) | 1.727 |
| 6,6'-di-(3-cyanophenyl)-2,2'-bis-(2-hydroxyethoxy)-1,1'-binaphthyl (compound Ia. 5) | 1.70 |
| 6,6'-di-(dibenzo[b,d]furan-4-yl)-2,2'-bis-(2-hydroxyethoxy)-1,1'-binaphthyl (compound Ia. 6) | 1.82 [2] |
| 6,6'-di-(dibenzo[b,d]thien-4-yl)-2,2'-bis-(2-hydroxyethoxy)-1,1'-binaphthyl (compound Ia. 7) | 1.84 [2] |
| 9,9-bis(4-(2-hydroxyethoxy)phenyl)fluorene [3] | 1.639 |
| Bisphenol A [3] | 1.589 |

[1] Refractive index of the homopolycarbonate at wavelength of 589 nm
[2] Calculated ab initio using the software described above
[3] Reference compounds - $n_D$ values as reported in U.S. Pat. No. 9,360,593

The following examples serve as further illustration of the invention.

ABBREVIATIONS

DCM: dichloromethane
MEK: 2-butanone
MeOH: methanol
EtOH: ethanol
MTBE: methyl tert-butyl ether
RT: room temperature
TLC: thin layer chromatography
TMEDA: N,N,N',N'-tetramethylethylenediamine
Analytics:
$^1$H-NMR spectra were determined at 23° C. using a 400 MHz NMR-spectrometer Avance III 400 HD from Bruker BioSpin GmbH. If not stated otherwise the solvent was CDCl$_3$ IR spectra were recorded by ATR FT-IR, using a Shimadzu FTIR-8400S spectrometer (45 no. of scans, resolution 4 cm$^{-1}$; apodization: Happ-Genzel).

Melting points of the compounds were determined by Buchi Melting Point B-545.

UPLC (Ultra Performance Liquid Chromatography) analyses were carried out using the following system and conditions:

Waters Acquity UPLC H-Class Systems; column: Acquity UPLC BEH C18, 1.7 µm, 2×100 mm; column temperature: 40° C., gradient: acetonitrile/water; injection volume: 0.4 µl; run time: 8 min; detection at 210 nm.

The yellowness index YI of the compounds of formula (I) can be determined by analogy to ASTN E313 using the following protocol: 1 g of the compound of formula (I) is dissolved in 19 g of a mixture of MEK/water 95:5 (v/v). The solution is transferred into a 50 mm cuvette and transmission is determined in the range 300-800 nm by a Shimadzu UV-Visible spectrophotometer UV-1650PC. A mixture of methyl ethyl ketone/water 95:5 (v/v) is used as a reference. From the spectra the yellowness index can be calculated by using the Software "RCA-software UV2DAT" in accordance with ASTM E308 (Standard practice for computing the colors of objects by using the CIE System) und ASTM E 313 (Standard practice for calculating yellowness and whiteness indices from instrumentally measured color coordinates).

The haze can be determined by measuring the transmission at 860 nm of a 5% solution of the respective compound of formula (I) in a mixture of methyl ethyl ketone/water 95:5 (v/v) by a standard nephelometer.

The refractive indices of the compounds of examples 8 and 9 were calculated by using the computer software ACD/ChemSketch 2012 (Advanced Chemistry Development, Inc.).

PREPARATION EXAMPLES

Example 1: Preparation of 6,6'-diphenyl-2,2'-bis-(2-hydroxyethoxy)-1,1'-binaphthyl (Compound of Formula (Ia.1)—Procedure 1

1.1: Preparation of 6,6'-dibromo-1,1'-bi-2-naphthol (Compound III 155 g (541.34 mmol) of 1,1'-bi-2-naphthol (compound II) was suspended in 2.6 L DCM under argon atmosphere and the suspension was cooled to a temperature of −78° C. 2.3 to 2.5 equivalents of bromine, either neat or as a solution in DCM, was then added dropwise over a period of about 2 hours to the suspension. After continued stirring for about 1 hour at 22° C., TLC analysis (mobile phase: MTBE/n- heptane 2:1 (v/v)) revealed approximately complete consumption of the starting material and the reaction was then quenched by the addition of 1.16 kg of a saturated aqueous solution of sodium metabisulfite. Following phase separation the organic phase was washed with brine, dried over sodium sulfate and concentrated with a rotary evaporator until the product started to precipitate. After the precipitation was completed, the obtained solids were filtered off, washed with ice-cold toluene and dried. By concentrating the mother liqueur further product was obtained, which was also filtered off, washed with ice-cold toluene and dried. Combining the product fractions resulted in 205-210 g (ca. 85.3%-87.3%) of the raw title compound.

1.2: Alternative Preparation of 6,6'-dibromo-1,1'-bi-2-naphthol (Compound III) Via Oxidative Coupling To a solution of 6-bromo-2-naphthol (750 g; 3.36 mol) in methanol (750 g) was added 5.5 g copper(II) chloride and 7.5 g TMEDA. The mixture was heated to 35° C. and a stream of air is passed through the mixture for 36 h under stirring. The mixture was cooled to 20° C. and the solid product was filtered off, washed with methanol and dried to yield 529 g (1.19 mol) of the title compound (71%) having a chemical purity of about 97% (UPLC). The mother liquor was concentrated, the precipitate filtered off and the obtained filter cake washed and dried to yield another 164 g with a chemical purity of about 90% (UPLC).

The obtained product could be further purified by recrystallization from toluene.

1.3: Alternative Preparation of 6,6'-dibromo-1,1'-bi-2-naphthol (Compound III 44.87 g of 1,1'-bi-2-naphthol was suspended in 350 mL (305 g) isopropyl acetate under an atmosphere of argon and the mixture was cooled to 0° C. Bromine (76.71 g) was then slowly added over a period of about 1 h in such a manner that the temperature did not rise above 5° C. Following the addition of bromine the reaction mixture was allowed to warm to room temperature. After the conversion was complete (approximately 2 h), the now homogeneous mixture was cooled down to 0° C. and a solution of $Na_2S_2O_5$ (25 g) in water (100 mL) was added to remove remaining bromine. The phases were separated and the organic phase was washed consecutively with water (60 mL), with a saturated aqueous solution of $Na_2CO_3$ (120 mL) until the pH value of the aqueous phase remained above 7, and with brine (50 mL). The organic phase was then dried over $Na_2SO_4$ and the solvent was removed in vacuo to yield 78.4 g of 6,6'-dibromo-1,1'-bi-2-naphthol as a brownish solid having a chemical purity of 91% (UPLC). This raw product was crystallized from a 2.5- to 3.5-fold volume of toluene and thoroughly washed with pentane to afford 58.3 g of the title compound (yellowish to white crystals) with a chemical purity of 98.8% (UPLC). Recrystallization from a 4.2- to 4.6-fold volume of toluene followed by thoroughly washing with pentane resulted in 54.4 g of the title compound (white crystals) having a chemical purity of 99.5% (UPLC).

1.4: Preparation of 6,6'-diphenyl-1,1'-bi-2-naphthol (Compound VII, with Ar=Phenyl 222.06 g (500 mmol) of 6,6'-dibromo-1,1'-bi-2-naphthol (compound III) obtained according to protocol 1.1, 152.41 g (1.25 mol) of phenylboronic acid (2.5 equivalents) and 7.61 g (25 mmol) of tri(o-tolyl)phosphine (3 mol-%) were charged to the reaction vessel under argon, and then 500 mL of a 2.0 M aqueous solution of potassium carbonate, 1350 mL (1.17 kg) of toluene and 1350 mL (1.07 kg) Ethanol [a toluene/EtOH mixture (1:1, v/v)] were added. The mixture was degassed and, after the addition of 1.13 g (5 mmol) of palladium(II) acetate (1 mol-%), was stirred under inert gas for about 1 to 3 hours at a temperature of 90° C. until TLC analysis (mobile phase: DCM/MTBE/n-heptane 20:1:5 (v/v/v)) revealed approximately complete consumption of the starting material. Reaction mixture was cooled down to RT and then diluted with 500 mL saturated $K_2CO_3$ aqueous solution/1 L water/1 L MEK, and mixture was stirred for 1 h. After aqueous phase separation, the organic phase was separated, washed with brine, mixed with MEK and the homogeneous solution was purified with activated charcoal, filtered through Celite® in order to remove traces of palladium. The filtrate was concentrated with a rotary evaporator (at 60° C. and up to 180 mbar) until solid precipitates. Suspension was cooled down to RT and stirred at this temperature for 1-2 hours. The precipitated solids were filtered off, washed with ice-cold toluene and dried to yield 167-202 g of the raw title compound (ca. 77-92%). Purification of a crude product by slurry wash in toluene at 80-90° C. for 3-4 hours gave 160-165 g of the purified product (ca. 73-75%).

1.5: 6,6'-diphenyl-2,2'-bis-(2-hydroxyethoxy)-1,1'-binaphthyl (Compound Ia.1

150.0 g (342 mmol) of 6,6'-diphenyl-1,1'-bi-2-naphthol, 90.37 g (1.026 mol) of ethylene carbonate (3 equiv.) and 14.18 g (102.6 mmol) of potassium carbonate (30 mol-%) in 900 g (1.04 L) toluene were heated under reflux for at least 5 hours (Caution: $CO_2$ gas evolution!), while monitoring the reaction progress by TLC (mobile phase: acetyl acetate or MTBE). Then mixture was cooled down to 70° C., addition amount of toluene (300-400 mL) was added and 150 mL water was then slowly added to the mixture. Caution: $CO_2$ gas evolution! After completion of a gas evolution and phase separation, the organic phase was washed successively twice with 5% aqueous solution of sodium hydroxide and twice or more with water until aqueous wash solution is neutral (pH=7). The organic phase was then concentrated with a rotary evaporator until the product started to precipitate. Following complete precipitation at RT, obtained solids were filtered off, washed with toluene and dried to afford 149-158 g of the raw title compound (yield: 82.7-87.7% and purity of ca. 87-90%). Two consecutive recrystallizations from toluene or from MEK gave 110-124 g of the purified title compound (ca. 61-69%) with a purity of >99% (UPLC).

Melting point: 162 to 164° C.

Example 2: Preparation of 6,6'-diphenyl-2,2'-bis-(2-hydroxyethoxy)-1,1'-binaphthyl (Compound of Formula (Ia.1)—Procedure 2

2.1: 6,6'-dibromo-2,2'-bis-(2-hydroxyethoxy)-1,1'-binaphthyl (compound IV, with X=1,2-ethandiyl 71.1 g (160 mmol) of 6,6'-dibromo-1,1'-bi-2-naphthol (compound III) obtained according to protocol 1.1, 42.27 g (480 mmol) of ethylene carbonate (3 equiv.) and 6.634 g (48 mmol) of potassium carbonate (30 mol-%) in 360 g (415 mL) toluene were heated under reflux for at least 5 hours (caution: $CO_2$ gas evolution!), while monitoring the reaction progress by TLC (mobile phase: acetyl acetate or MTBE).

Afterwards the reaction mixture was cooled to 80° C., additional 300 mL MEK was added to dissolve precipitated solids and obtain a clear solution. Then 150 mL of water were slowly added to the reaction mixture (caution: gas evolution!). After completion of the gas evolution and phase separation, the organic phase was washed successively twice with 5% or 10% aqueous solution of sodium hydroxide and twice or more with water until the aqueous wash solution was neutral (pH=7). The organic phase was then concentrated with a rotary evaporator until the product started to precipitate. Following complete precipitation the obtained solids were filtered off, washed with toluene and dried to afford 17.1 g of the raw title compound (ca. 80.3%).

2.2: Alternative preparation of 6,6'-dibromo-2,2'-bis-(2-hydroxyethoxy)-1,1'-binaphthyl (Compound IV, with X=1,2-ethandiyl To a mixture of 70 g (157 mmol) of 6,6'-dibromo-1,1'-bi-2-naphthol, 452 g anisole and 6.5 g (47 mmol) of potassium carbonate (30 mol-%) was added 41.6 g (473 mmol) of ethylene carbonate (3 equiv.) and the mixture was heated under reflux for at least 1 h (caution: $CO_2$ gas evolution!), while monitoring the reaction progress by TLC (mobile phase: MTBE). Afterwards the reaction mixture was cooled to 80° C. and 50 mL of water and 19 g of brine were slowly added (caution: gas evolution!). After completion of the gas evolution and phase separation, the organic phase was treated with a 15% aqueous solution of sodium hydroxide for 1 h. After separation of the aqueous phase the organic phase was washed twice or more with a diluted aqueous solution of NaCl until the aqueous wash solution was neutral (pH=7). The organic phase was used directly for the next reaction step (see protocol 2.4 below).

2.3: 6,6'-diphenyl-2,2'-bis-(2-hydroxyethoxy)-1,1'-binaphthyl (Compound Ia.1

212.89 g (400 mmol) of 6,6'-dibromo-2,2'-bis-(2-hydroxyethoxy)-1,1'-binaphthyl, 121.93 g (1 mol) of phenylboronic acid (2.5 equivalents) and 6.087 g (20 mmol) of tri(o-tolyl)-phosphine (5 mol-%) were charged to the reaction vessel under argon, and then 400 mL of a 2.0 M aqueous solution of potassium carbonate and 2.16 L of a toluene/EtOH mixture (1:1, v/v) were added. The mixture was degassed and, after the addition of 900 mg (4 mmol) of palladium(II) acetate (1 mol-%), was stirred under inert gas for 1 to 3 hours at a temperature of 90° C. until TLC analysis (mobile phase: MeOH/$H_2O$=7:3 (v/v)) revealed approximately complete consumption of the starting material. The reaction mixture was cooled down to RT and then diluted with 500 mL saturated aqueous solution of $K_2CO_3$, 1 L water and 1 L MEK, and the obtained mixture was stirred for 1 h. The organic phase was separated, washed subsequently with 500 mL of a 2 M aqueous solution of HCl, 500 mL brine, and the resulting homogeneous solution was purified with activated charcoal (ca. 10 g) and filtered through Celite® in order to remove traces of palladium. Solvent was removed with a rotary evaporator to obtain a viscous oil, which was dried in vacuo to remove volatiles. Toluene (ca. 180-200 g) was then added and the mixture was homogenized under reflux. The obtained solution was slowly cooled down to RT, while solid material precipitated. The suspension was stirred at RT for more than 12 hours, while the product very slowly crystalized. The precipitated solids were then filtered off, washed with ice-cold toluene and dried to yield 161-185 g of the raw title compound (ca. 76-88% with a purity of 81-87%). The crude product was purified by slurry wash in MeOH followed by recrystallization from MEK to give 145-150 g of the purified product (ca. 69-71%) having a purity of >99.5% (UPLC).

2.4: Alternative preparation of 6,6'-diphenyl-2,2'-bis-(2-hydroxyethoxy)-1,1'-binaphthyl (Compound Ia.1

To the organic phase obtained according to protocol 2.2 40.4 g of phenylboronic acid, 73.6 g of $K_3PO_4$, 163.5 g of water and 192 mg of tri(o-tolyl)-phosphine were added. The mixture was heated to 60° C. and 35 mg of palladium(II) acetate (0.1 mol-%) were added. The exothermic reaction effected a temperature increase to 95° C. The mixture was then heated to reflux for 15 min and afterwards cooled to 70° C. The organic phase was washed successively with a diluted aqueous solution of NaOH (5%; 200 mL), with a 4 M aqueous solution of HCl (63 mL) and with brine (200 mL). The organic phase was then treated with activated charcoal, dried over $Na_2SO_4$ (40 g) and filtered through Celite®. The solvent was removed under reduced pressure and the residue was taken up in a hot mixture of toluene and methanol (3:7 (v/v); 85 g). The resulting mixture was cooled to RT and stirred overnight. The formed crystals were collected by filtration, washed with pentane and dried at 60° C. to yield 70.8 g of the title compound with a chemical purity of 96.7% (UPLC).

Example 3: Preparation of 6,6'-diphenyl-2,2'-bis-(2-hydroxyethoxy)-1,1'-binaphthyl (Compound of Formula (Ia.1)—Procedure 3

3.1: 2,2'-bis-(2-hydroxyethoxy)-1,1'-binaphthyl (compound VIII, with X=1,2-ethandiyl 150.0 g (523.88 mmol) of 1,1'-bi-2-naphthol (compound II), 138.37 g (1571.3 mmol) of ethylene carbonate (3 equiv.) and 21.75 g (157.13 mmol) of potassium carbonate (30 mol-%) in 1 L toluene were heated under reflux for at least 5 to 6 hours, by maintaining argon atmosphere. During the reaction gas evolves. The reaction is monitored by TLC using TBME as solvent. When TLC indicates complete reaction the slightly yellow reaction mixture is cooled to 70° C. and mixed with 100 g of water (Caution: $CO_2$ gas evolution!) The reaction mixture is then stirred for further 10-15 min at 70° C. to dissolve potassium carbonate. The stirrer is stopped and phases are separated at about 70° C. The organic phase is washed with 100 g of 5% w/w aqueous solution of NaOH at 80-90° C. for at least 1 h (Caution: $CO_2$ gas evolution!), followed by washing with water (each 100 mL) at 70° C., until the pH of the washing water is neutral (pH 7). 15 g of charcoal is optionally added to the organic phase and the mixture is stirred at 70° C. for 30 min. Then the warm solution is filtered through Celite®. The clear and slightly yellowish filtrate is cooled to RT and product crystallizes in the form of thin platelets. The solid is filtered off, washed with toluene and dried. 142-170 g (72.4-86.7%) of the title compound are obtained as a white, dry solid.

3.2: 6,6'-dibromo-2,2'-bis-(2-hydroxyethoxy)-1,1'-binaphthyl (Compound IV, with X=1,2-ethandiyl A suspension of 37.44 g (100 mmol) of 2,2'-bis-(2-hydroxyethoxy)-1,1'-binaphthyl in 485 mL DCM was cooled to a temperature of −10° C. 40 g Bromine (2.3 to 2.5 equivalents) as a solution in DCM (120 mL) were then added dropwise over a period of between 1 and 2 hours to the suspension. After continued stirring for about 1 to 2 hours at RT, TLC analysis (mobile phase: MTBE/n-heptane 2:1 (v/v) or MeOH/water 7:3 (v/v)) revealed approximately complete consumption of the starting material and the reaction was then quenched by the addition of aqueous solution of sodium metabisulfite (12 g of $Na_2S_2O_5$ dissolved in 50 g water). Since product slowly precipitates, additionally 2.35 L MEK and 750 mL water were added in order to homogenize both organic and aqueous layers and to obtain two clear phases. Following phase separation the organic phase was successively washed with water (500 g), then saturated $Na_2CO_3$-solution (80 mL) [gas evolution] and brine (500 mL), dried over magnesium sulfate. The dried organic phase was filtered through Celite® and concentrated with a rotary evaporator until the product started to precipitate. After the precipitation was completed the obtained solids were filtered off, washed with ice-cold toluene and dried. By concentrating the mother liqueur further product was obtained, which was also filtered off, washed with ice-cold toluene and dried. Combined the product fractions were suspended in MTBE and purified twice by slurry wash at 45-50° C. for 2 hours, finally resulting in 44.5 g g of the purified title compound (83%), which was used without additional recrystallization for the next step.

3.3: Alternative preparation of 6,6'-dibromo-2,2'-bis-(2-hydroxyethoxy)-1,1'-binaphthyl (Compound IV, with X=1,2-ethandiyl 44.9 g of 2,2'-bis-(2-hydroxyethoxy)-1,1'-binaphthyl were suspended under argon or nitrogen in 250 mL MEK at a temperature of 20-22° C. To the suspension were added 100 mg of ammonium acetate (about 1.5 mol-%) as catalyst and a suspension of 48.1 g of N-bromosuccinimide (2.1-2.2 equiv.) in 500 mL of MEK. The reaction mixture turned into a reddish solution and was stirred for another 1 to 2 hours until TLC analysis showed approximately complete consumption of the starting material. The reaction was then quenched by the addition of 25 mL of a saturated aqueous solution of sodium metabisulfite. Following phase separation the organic phase was washed successively with water and brine, dried over sodium sulfate and concentrated with a rotary evaporator until the product started to precipitate. Then 300 mL of water were added and the residual MEK was removed in the rotary evaporator at a temperature of 60° C. The obtained solids were slurried in the remaining water at a temperature of 60° C. and filtered off. The solids were slurried again in 300 mL of water at 60° C., filtered off and washed with water and dried in an oven at a temperature of 60° C. overnight. Further washing was achieved by slurrying the solids in 337 mL of MTBE at a temperature of 45° C. After cooling the slurry to RT the solids were filtered off, washed with MTBE and dried to afford 40.0 g of the title compound (63%) with a chemical purity of 77.25% (UPLC).

3.4: Alternative preparation of 6,6'-dibromo-2,2'-bis-(2-hydroxyethoxy)-1,1'-binaphthyl (Compound IV, with X=1,2-ethandiyl In a reaction vessel, which had previously been dried and flushed with nitrogen or argon, 44.9 g of 2,2'-bis-(2-hydroxyethoxy)-1,1'-binaphthyl were suspended under argon or nitrogen in 337 mL of dry THF (peroxides-free and stabilized) at a temperature of 20-22° C. To the suspension were added 43.5 g of N-bromosuccinimide (2.1-2.2 equiv.) as a solid in four portions over 1.5 h. The reaction mixture turned into a yellow solution and was stirred overnight after which TLC analysis showed approximately complete consumption of the starting material. The reaction was then quenched by the addition of 25 mL of a saturated aqueous solution of sodium metabisulfite. Following phase separation the organic phase was washed successively with water and brine, dried over sodium sulfate and concentrated with a rotary evaporator until the product started to precipitate. Then 300 mL of water were added and the residual THF was removed in the rotary evaporator at a temperature of 60° C. The obtained solids were slurried in the remaining water at a temperature of 60° C., filtered off, washed with water and dried in an oven at a temperature of 60° C. and filtered off. The solids were slurried again in 300 mL of water at 60° C., filtered off and washed with water and dried in an oven at a temperature of 60° C. overnight. Further washing was achieved by slurrying the solids in 337 mL of MTBE at a temperature of 45° C. After cooling the slurry to RT the solids were filtered off, washed with MTBE and dried to afford 57.2 g of the title compound (90%) with a chemical purity of 91.34% (UPLC).

3.5: 6,6'-diphenyl-2,2'-bis-(2-hydroxyethoxy)-1,1'-binaphthyl (Compound Ia.1

212.89 g (400 mmol) of 6,6'-dibromo-2,2'-bis-(2-hydroxyethoxy)-1,1'-binaphthyl, 121.93 g (1 mol) of phenylboronic acid (2.5 equivalents) and 6.087 g (20 mmol) of tri(o-tolyl)phosphine (5 mol-%) were charged to the reaction vessel under argon, and then 400 mL of a 2.0 M aqueous solution of potassium carbonate and 2.16 L of a toluene/EtOH mixture (1:1, v/v) were added. The mixture was degassed and, after the addition of 900 mg (4 mmol) of palladium(II) acetate (1 mol-%), was stirred under inert gas for 1 to 3 hours at a temperature of 90° C. until TLC analysis (mobile phase: $MeOH/H_2O=7:3$ (v/v)) revealed approximately complete consumption of the starting material. The reaction mixture was cooled to RT and then diluted with 500 mL saturated $K_2CO_3$ aqueous solution, 1 L water and 1 L MEK, and the mixture was then stirred for 1 h. After phase separation the organic phase was isolated, washed successively with 500 mL of 2M HCl, 500 mL of brine, and the resulting homogeneous solution was purified with activated charcoal (about 10 g) and filtered through Celite® in order to remove traces of palladium. Solvent was removed with a rotary evaporator to obtain a viscous oil, which was dried in vacuo to remove volatiles. Toluene (ca. 180-200 g) was then added and the mixture was homogenized under reflux. The obtained solution was slowly cooled to RT, while solid precipitated. The thus obtained suspension was stirred at RT for more than 12 hours, while the product very slowly crystalized. The precipitated solids were then filtered off, washed with ice-cold toluene and dried to yield 161-185 g of the raw title compound (ca. 76-88%) with a purity of 81-87% (UPLC). The crude product was purified by slurry wash in MeOH followed by recrystallization from MEK to give 145-150 g of the purified title compound (ca. 69-71%) having purity of >99.5% (UPLC).

$^1$H NMR (400 MHz, $CDCl_3$): δ=8.12 (d, J=1.7 Hz, 2H), 8.06 (d, J=9.0 Hz, 2H), 7.75-7.65 (m, 4H), 7.60-7.43 (m, 8H), 7.40-7.32 (m, 2H), 7.31-7.23 (m, 2H), 4.27 (ddd, J=10.0, 6.6, 2.7 Hz, 2H), 4.07 (ddd, J=10.3, 5.4, 2.7 Hz, 2H), 3.66 (ddd, J=12.4, 5.4, 2.7 Hz, 2H), 3.59 (ddd, J=12.4, 6.6, 2.7 Hz, 2H), 2.44 (br s, 2H) ppm.

IR [$cm^{-1}$]: 819.77, 825.56, 835.21, 850.64, 864.14, 885.36, 896.93, 941.29, 983.73, 1037.74, 1053.17, 1082.10, 1149.61, 1201.69, 1217.12, 1247.99, 1282.71, 1340.57, 1361.79, 1375.29, 1442.80, 1492.95, 1575.89, 1595.18, 1622.19, 2870.17, 2933.83, 2972.40, 3319.60.

Melting point: 164° C.

Example 4: Preparation of 6,6'-di-(1-naphthyl)-2,2'-bis-(2-hydroxyethoxy)-1,1'-binaphthyl (Compound Ia.2

6,6'-dibromo-2,2'-bis-(2-hydroxyethoxy)-1,1'-binaphthyl (compound IV, with X=1,2-ethandiyl) and 1-naphthylboronic acid (2.5 equivalents) were reacted in accordance with the protocol of example 2.3. Workup of the reaction mixture and recrystallization of the raw product gave the title compound in 74% yield. The purity of the obtained product was >99% (UPLC).

$^1$H NMR (400 MHz, CDCl$_3$): δ=8.11-8.03 (m, 4H), 7.99 (d, J=8.4 Hz, 2H), 7.93 (d, J=8.1 Hz, 2H), 7.89 (d, J=7.4 Hz, 2H), 7.60-7.46 (m, 10H), 7.46-7.40 (m, 2H), 7.37 (d, J=8.7 Hz, 2H), 4.38-4.28 (m, 2H), 4.21-4.09 (m, 2H), 3.88-3.54 (m, 4H), 2.50 (t, J=6.4, 2H) ppm.

IR [cm$^{-1}$]: 802.41, 831.35, 864.14, 889.21, 937.44, 962.51, 987.59, 1018.45, 1049.31, 1082.1, 1095.60, 1112.96, 1145.75, 1207.48, 1238.34, 1251.84, 1280.78, 1334.78, 1394.58, 1454.38, 1483.31, 1575.89, 1591.33, 1624.12, 2874.03, 2920.32, 3045.70, 3383.26.

Melting point: 220° C.

Example 5: Preparation of 6,6'-di-(2-naphthyl)-2,2'-bis-(2-hydroxyethoxy)-1,1'-binaphthyl (Compound Ia.3

6,6'-dibromo-2,2'-bis-(2-hydroxyethoxy)-1,1'-binaphthyl (compound IV, with X=1,2-ethandiyl) and 1-naphthylboronic acid (2.5 equivalents) were reacted in accordance with the protocol of example 2.3. Workup of the reaction mixture and recrystallization of the raw product from acetone gave the title compound in 86% yield. The purity of the obtained product was >99% (UPLC).

$^1$H NMR (400 MHz, CDCl$_3$): δ=8.25 (d, J=1.8 Hz, 2H), 8.13 (d, J=1.3 Hz, 2H), 8.10 (d, J=9.0 Hz, 2H), 7.98-7.81 (m, 8H), 7.68 (dd, J=8.8, 1.9 Hz, 1H), 7.60-7.42 (m, 6H), 7.32 (d, J=8.8 Hz, 2H), 4.29 (ddd, J=10.3, 6.6, 2.8 Hz, 2H) 4.10 (ddd, J=10.4, 5.4, 2.7 Hz, 2H), 3.68 (ddd, J=12.4, 5.4, 2.7 Hz, 2H), 3.61 (ddd, J=12.4, 6.6, 2.7 Hz, 2H), 2.11 (br s, 2H) ppm.

IR [cm$^{-1}$]: 800.49, 815.92, 835.21, 864.14, 879.57, 931.65, 952.87, 1014.59, 1028.09, 1049.31, 1097.53, 1143.83, 1201.69, 1228.70, 1246.06, 1296.21, 1329.00, 1359.86, 1394.58, 1435.09, 1460.16, 1479.45, 1572.04, 1585.54, 1618.33, 1979.03, 2955.04, 3053.42, 3495.13, 3574.21.

Melting point: 199° C.

Example 6: Preparation of 6,6'-di-(9-phenanthryl)-2,2'-bis-(2-hydroxyethoxy)-1,1'-binaphthyl (Compound Ia.4

6,6'-dibromo-2,2'-bis-(2-hydroxyethoxy)-1,1'-binaphthyl (compound IV, with X=1,2-ethandiyl) and 9-phenanthrylboronic acid (2.5 equivalents) were reacted in accordance with the protocol of example 2.3. Workup of the reaction mixture and recrystallization of the raw product from tetrahydrofurane gave the title compound in 88% yield. The purity of the obtained product was >99% (UPLC).

$^1$H NMR (400 MHz, CDCl$_3$): δ=8.79 (d, J=8.2 Hz, 2H), 8.74 (d, J=8.2 Hz, 2H), 8.10 (d, J=1.5 Hz, 2H), 8.08 (d, J=9.0 Hz, 2H), 8.01 (d, J=7.5 Hz, 2H), 7.91 (dd, J=7.8, 1.2 Hz, 2H), 7.80 (s, 2H), 7.72-7.58 (m, 6H), 7.58-7.50 (m, 6H), 7.40 (d, J=8.7 Hz, 2H), 4.34 (ddd, J=10.1, 6.2, 2.8, 2H), 4.17 (ddd, J=10.3, 5.4, 2.7 Hz, 2H), 3.83-3.64 (m, 4H), 2.09 (br s, 2H) ppm.

IR [cm$^{-1}$]: 702.11, 725.26, 750.33, 767.69, 792.77, 808.20, 831.35, 854.49, 889.21, 929.72, 954.80, 968.30, 995.30, 1051.24, 1087.89, 1128.39, 1166.97, 1192.05, 1247.99, 1271.13, 1307.78, 1334.78, 1423.51, 1450.52, 1481.38, 1591.33, 2872.10, 2933.83, 3400.62.

Melting point: 257° C.

Example 7: Preparation of 6,6'-di-(3-cyanophenyl)-2,2'-bis-(2-hydroxyethoxy)-1,1'-binaphthyl (Compound Ia.5

87.3 g (160 mmol) of 6,6'-dibromo-2,2'-bis-(2-hydroxyethoxy)-1,1'-binaphthyl (compound IV, with X=1,2-ethandiyl), 49.4 g (336 mmol) of 3-cyanophenyl-boronic acid (2.1 equivalents), 74.7 g of K$_3$PO$_4$ (352 mmol), 165 g of water, 472 mL of toluene, 472 mL of ethanol and 390 mg of tri(o-tolyl)-phosphine (1.3 mmol) were charged to the reaction flask under argon. The mixture was heated to 60° C. and following the addition of 72 mg (0.32 mmol) of palladium(II) acetate (0.2 mol-%) was stirred under reflux for 2.5 hours until TLC analysis (mobile phase: methanol/water=3:1 (v/v)) showed complete conversion. The reaction mixture was then cooled down to 60° C. and the organic phase was separated, mixed with 400 mL of MEK and 200 mL of water, and the resulting mixture was stirred for 5 min. The water phase was removed and the organic phase was successively washed with a 8% aqueous solution of NaOH (200 mL), with a 4 M aqueous HCl (100 mL) and with brine (100 mL). The organic phase was cooled to 20° C. and stirred overnight. The formed precipitate was collected by filtration, washed with pentane and dried (at 60° C.) to yield 84.6 g of the raw title compound (88%) having a chemical purity of 96.2% (UPLC). This material was further purified by recrystallization from toluene/acetonitrile (1:1 (v/v); 514 g) to yield 72.2 g of crystalline title compound with a chemical purity of 97.7% (UPLC).

$^1$H NMR (400 MHz, DMSO-d$_6$): δ=8.40 (d, J=1.9 Hz, 2H), 8.25 (t, J=1.8 Hz, 2H), 8.20-8.14 (m, 2H), 8.11 (ddd, J=8.0, 1.9, 1.1 Hz, 2H), 7.83 (dt, J=7.7, 1.3 Hz, 2H), 7.74-7.60 (m, 6H), 7.03 (d, J=8.9 Hz, 2H), 4.64 (t, J=5.3 Hz, 2H), 4.13-4.03 (m, 4H), 3.44 (q, J=5.4 Hz, 4H).

Melting point: 208 to 209° C.

Example 8: Preparation of 6,6'-di-(dibenzo[b,d]thien-4-yl)-2,2'-bis-(2-hydroxyethoxy)-1,1'-binaphthyl (Compound Ia.7

43.8 g (80 mmol) of 6,6'-dibromo-2,2'-bis-(2-hydroxyethoxy)-1,1'-binaphthyl (compound IV, with X=1,2-ethandiyl), 40.33 g (168 mmol) of dibenzothiophene-4-boronic acid (2.1 equivalents), 37.4 g of K$_3$PO$_4$ (176 mmol), 83 g of water, 236 mL of toluene, 236 mL of ethanol and 97.4 mg of tri(o-tolyl) phosphine (0.32 mmol) were charged to the reaction vessel under argon. The mixture was heated to 60° C. and, after the addition of 18 mg (0.08 mmol) of palladium(II) acetate (0.1 mol-%), was stirred under reflux for 6 hours until TLC analysis (mobile phase: ethyl acetate/dichloromethane=1:1 (v/v)) showed complete conversion. The reaction mixture was cooled down to 60° C. and the aqueous phase was removed. The organic phase was cooled to room temperature and the formed precipitate was collected by filtration. The mother liquor was concentrated and additional precipitate was collected by filtration. The combined filter cakes were washed successively with water (200 mL), with a 20% aqueous solution of NaOH (200 mL) and again two times with water (2×200 g) to yield the 42 g of the title compound (70%) with a chemical purity of 98.2% (UPLC).

$^1$H NMR (400 MHz, DMSO-d$_6$): δ=8.45-8.35 (m, 6H), 8.20 (d, J=9.0 Hz, 2H), 8.04-7.95 (m 2H), 7.75 (d, J=9.2 Hz, 2H), 7.69-7.60 (m 6H), 7.58-7.47 (m 4H), 7.18 (d, J=8.8 Hz, 2H), 4.68 (t, J=5.3 Hz, 2H), 4.14 (td, J=5.5, 1.9 Hz, 4H), 3.51 (q, J=5.7 Hz, 4H).

Melting point: 214 to 216° C.

Example 9: Preparation of 6,6'-di-(dibenzo[b,d]furan-4-yl)-2,2'-bis-(2-hydroxyethoxy)-1,1'-binaphthyl (Compound Ia.6

89 g (160 mmol) of 6,6'-dibromo-2,2'-bis-(2-hydroxyethoxy)-1,1'-binaphthyl (compound IV, with X=1,2-ethandiyl), 75 g (336 mmol) of dibenzofuran-4-boronic acid (2.1 equivalents), 74.7 g of K$_3$PO$_4$ (352 mmol), 166 g of water, 472 mL of toluene, 472 mL of ethanol and 194.8 mg of tri(o-tolyl) phosphine (0.64 mmol) were charged to the reaction vessel under argon. The mixture was heated to 60° C. and, after the addition of 36 mg (0.16 mmol) of palladium (II) acetate (0.1 mol-%), was stirred under reflux for 0.5 hours until TLC analysis (mobile phase: ethyl acetate/dichloromethane=1:1 (v/v)) showed complete conversion. The reaction mixture was cooled down to 60° C. and the aqueous phase was removed. The organic phase was cooled to room temperature and precipitate was collected by filtration. The filter cake was washed with water (200 mL) and dried to yield 99.8 g of the title compound with a chemical purity of 95% (UPLC).

$^1$H NMR (400 MHz, DMSO-d$_6$): δ=8.52 (d, J=1.9 Hz, 2H), 8.26-8.10 (m, 6H), 7.85-7.75 (m, 4H), 7.77-7.70 (m, 4H), 7.58-7.47 (m, 4H), 7.42 (td, J=7.5, 1.0 Hz, 2H), 7.16 (d, J=8.9 Hz, 2H), 4.66 (t, J=5.3 Hz, 2H), 4.12 (td, J=5.3, 2.5 Hz, 4H), 3.50 (q, J=5.4 Hz, 4H).

Melting point range: 230 to 235° C.

Example 10: Preparation of diethyl 2,2'-{(6,6'-diphenyl[1,1'-binaphthalene]-2,2'-diyl)bis(oxy)}diacetate (Compound Id.1

6,6'-Diphenyl-1,1'-bi-2-naphthol (48.24 g, 110 mmol) and ethyl α-chloroacetate (40.31 g, 328.9 mmol) were dissolved in 1.2 L of dry acetone and anhydrous K$_2$CO$_3$ (37.85 g, 273.9 mmol) was added to the solution. The mixture was refluxed for 8-12 h and the conversion was monitored by TLC. After completion, the reaction mixture was cooled to RT and K$_2$CO$_3$ was filtered off. After evaporation of the solvent, water was added to the residue, and the mixture was then extracted with 3×20 mL methyl ethyl ketone or a mixture of toluene and methyl ethyl ketone (20:80%$_{v/v}$). The organic layers were collected, dried over anhydrous Na$_2$SO$_4$ or MgSO$_4$, and the solvent was evaporated. Yield of the title compound was 59.79 g (89%).

Example 11: Preparation of 2,2'-{(6,6'-diphenyl[1,1'-binaphthalene]-2,2'-diyl)bis(oxy)}diacetic Acid (Compound Ib.1

58.0 g (95 mmol) of compound Id.1 was mixed with 1 L of a 20% solution of KOH in ethanol-water (80:20%$_{v/v}$). The mixture was refluxed for 2-3 h and the reaction was monitored by TLC. After completion of the reaction, ethanol was evaporated, deionized water was added and the pH was finally adjusted to pH=1-2 with concentrated HCl. The precipitated solid was filtered off and dissolved in toluene and methyl ethyl ketone (20:80%$_2$/2). The solution dried over anhydrous Na$_2$SO$_4$ or MgSO$_4$ and then concentrated until the title compound crystallized. Precipitated solid was filtered off, washed with toluene and dried at 60-70° C. to yield 47.42 g of the title compound Ib.1 (yield 90%; chemical purity (UPLC): 98.7%)

$^1$H NMR (400 MHz, DMSO-d$_6$) δ 9.42 (br s, 2H), 8.25 (s, 2H), 8.19-8.09 (m, 2H), 7.74 (t, J=8.3 Hz, 4H), 7.63-7.42 (m, 8H), 7.41-7.30 (m, 2H), 7.15-7.05 (m, 2H), 4.74-4.59 (m, 4H).

We claim:

1. A compound of the formula (I)

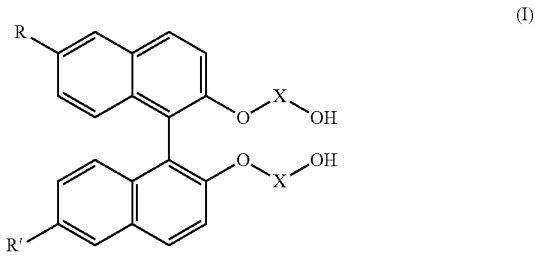

where
X is C$_2$-C$_4$-alkandiyl or C$_1$-C$_4$-alkandiyl-C(O)—, where C(O) is bound to the oxygen atom of the hydroxyl group and where C$_2$-C$_4$-alkandiyl or C$_1$-C$_4$-alkandiyl, respectively, are unsubstituted or carry a phenyl ring;
R and R' are identical or different and selected from mono- or polycyclic aryl having from 6 to 36 carbon atoms and mono- or polycyclic hetaryl having a total of 5 to 36 atoms, which are ring members, where 1, 2, 3 or 4 of these atoms are selected from nitrogen, sulfur and oxygen, while the remainder of these atoms are carbon atoms, where mono- or polycyclic aryl and mono- or polycyclic hetaryl are unsubstituted or carry 1 or 2 radicals R$^a$, which are selected from the group consisting of CN, CH$_3$, OCH$_3$, O-phenyl, O-naphthyl, S-phenyl, S-naphthyl and halogen,
and, if X is C$_1$-C$_4$-alkandiyl-C(O)—, the esters thereof.

2. The compound of claim 1, where R and R' are identical.

3. The compound of claim 1, where R and R' are identical or different and selected from mono- or polycyclic aryl having from 6 to 36 carbon atoms and mono- or polycyclic hetaryl having a total of 5 to 36 atoms, which are ring members, where 1, 2, 3 or 4 of these atoms are selected from nitrogen, sulfur and oxygen, while the remainder of these atoms are carbon atoms, where mono- or polycyclic aryl and mono- or polycyclic hetaryl are unsubstituted.

4. The compound of claim 1, where R and R' are selected from the group consisting of
azulenyl,
indenyl, which is unsubstituted or substituted by 1, 2, 3, 4 or 5 radicals selected from phenyl and polycyclic aryl bearing 2, 3 or 4 phenyl rings, which are linked to each other via a single bond, directly fused to each other and/or fused to a saturated or unsaturated 4- to 10-membered mono- or bicyclic hydrocarbon ring;
phenyl, which is unsubstituted;
phenyl, which is substituted by 1 or 2 CN radicals;
phenyl, which is substituted by 1, 2, 3, 4 or 5 radicals selected from phenyl and polycyclic aryl bearing 2, 3 or 4 phenyl rings, which are linked to each other via a single bond, directly fused to each other and/or fused to a saturated or unsaturated 4- to 10-membered mono- or bicyclic hydrocarbon ring; and polycyclic aryl bearing 2, 3 or 4 phenyl rings, which are directly fused to each other and/or fused to a saturated or unsaturated 4- to 10-membered mono- or bicyclic hydrocarbon ring, where polycyclic aryl is unsubstituted or substituted by 1 or 2 radicals selected from phenyl and polycyclic aryl bearing 2 or 3 phenyl rings, which are linked to each other via a single bond, directly fused to each other and/or fused to a saturated 4- to 10-membered mono- or bicyclic hydrocarbon ring, where the phenyl rings of polycyclic aryl are unsubstituted or carry 1 or 2 radicals $R^a$.

5. The compound of claim 1, where R and R' are selected from the group consisting of phenyl, which is unsubstituted or substituted by 1, 2, 3, 4 or 5 phenyl radicals, phenyl, which is substituted by 1 or 2 CN radicals, phenyl, which is substituted by 1 or 2 polycyclic aryl radicals selected from biphenyl, naphthyl, fluorenyl, anthracenyl, phenanthryl and pyrenyl and optionally by 1 further phenyl radical;

naphthyl, which is unsubstituted or substituted by 1 or 2 radicals selected from CN, phenyl and polycyclic aryl selected from biphenyl, naphthyl, fluorenyl, anthracenyl, phenanthryl and pyrenyl;

biphenylenyl;

triphenylenyl;

tetraphenylenyl;

phenanthryl;

pyrenyl;

9H-fluorenyl;

dibenzo[a,e][8]annulenyl;

perylenyl; and 9,9'-spirobi[9H-fluoren]yl.

6. The compound of claim 5, where R and R' are selected from the group consisting of phenyl, 2-cyanophenyl, 3-cyanophenyl, 4-cyanophenyl, 2-naphthyl, 1-naphthyl, and 9-phenanthryl.

7. The compound of claim 1, where R and R' are selected from the group consisting of heteroaromatic monocyclic radicals having 5 or 6 ring atoms, which comprise 1, 2, 3 or 4 nitrogen atoms or 1 oxygen atom and 0, 1, 2 or 3 nitrogen atoms or 1 sulfur atom and 0, 1, 2 or 3 nitrogen atoms, where the remainder of the ring atoms are carbon atoms, heteroaromatic polycyclic radicals, which bear a heteroaromatic monocycle as defined above and 1, 2, 3, 4 or 5 further aromatic rings selected from phenyl and heteroaromatic monocycles, where the (hetero)aromatic rings of polycyclic hetaryl are linked to each other by a covalent bond or fused to each other directly and/or fused to a saturated or unsaturated 4 to 10-membered mono- or bicyclic hydrocarbon ring; and heteroaromatic polycyclic radicals, which bear at least one saturated or partially unsaturated 5- or 6-membered heterocyclic ring bearing 1 or 2 heteroatoms selected from oxygen, sulfur and nitrogen as ring atoms, and 1, 2, 3, 4 or 5 further aromatic rings selected from phenyl and heteroaromatic monocycles as defined above, where at least one of the further aromatic rings is directly fused to the saturated or partially unsaturated 5- or 6-membered heterocyclic radical and where the remainder of further aromatic rings of polycyclic hetaryl are linked to each other by a covalent bond or fused to each other directly and/or fused to a saturated or unsaturated 4 to 10-membered mono- or bicyclic hydrocarbon ring.

8. The compound of claim 7, where R and R' are selected from the group consisting of furyl, thienyl, pyrrolyl, imidazolyl, pyrazolyl, 1,2,3-triazolyl, 1,2,4-triazolyl, tetrazolyl, oxazolyl, isoxazolyl, 1,3,4-oxadiazolyl, 1,2,4-oxadiazolyl, pyridyl, pyrazinyl, pyridazinyl, pyrimidinyl, triazinyl, benzofuryl, dibenzofuranyl, benzothienyl, dibenzothienyl, thianthrenyl, naphthofuryl, furo[3,2-b]furanyl, furo[2,3-b]furanyl, furo[3,4-b]furanyl, oxanthrenyl, indolyl, isoindolyl, carbazolyl, indolizinyl, benzopyrazolyl, benzimidazolyl, benzoxazolyl, benzo[cd]indolyl, 1H-benzo[g]indolyl, quinolinyl, isoquinolinyl, acridinyl, phenazinyl, quinazolinyl, quinoxalinyl, phenoxazinyl, benzo[b][1,5]naphthyridinyl, cinnolinyl, 1,5-naphthyridinyl, 1,8-naphthyridinyl, phenylpyrrolyl, naphthylpyrrolyl, dipyridyl, phenylpyridyl, naphthylpyridyl, pyrido[4,3-b]indolyl, pyrido[3,2-b]indolyl, pyrido[3,2-g]quinolinyl, pyrido[2,3-b][1,8]naphthyridinyl, pyrrolo[3,2-b]pyridinyl, pteridinyl, puryl, 9H-xanthenyl, 2H-chromenyl, phenanthridinyl, phenanthrolinyl, furo[3,2-f][1]benzofuranyl, furo[2,3-f][1]benzofuranyl, furo[3,2-g]quinolinyl, furo[2,3-g]quinolinyl, furo[2,3-g]quinoxalinyl, benzo[g]chromenyl, pyrrolo[3,2,1-hi]indolyl, benzo[g]quinoxalinyl, benzo[f]quinoxalinyl, and benzo[h]isoquinolinyl.

9. The compound of claim 1, where X is $C_2$-$C_4$-alkandiyl.

10. The compound of claim 1, where X is $C_1$-$C_4$-alkandiyl-C(O)—.

11. The compound of claim 1, which is selected from the group consisting of 6,6'-diphenyl-2,2'-bis-(2-hydroxyethoxy)-1,1'-binaphthyl, 6,6'-di-(1-naphthyl)-2,2'-bis-(2-hydroxyethoxy)-1,1'-binaphthyl, 6,6'-di-(2-naphthyl)-2,2'-bis-(2-hydroxyethoxy)-1,1'-binaphthyl 6,6'-di-(9-phenanthryl)-2,2'-bis-(2-hydroxyethoxy)-1,1'-binaphthyl, 6,6'-di-(3-cyanophenyl)-2,2'-bis-(2-hydroxyethoxy)-1,1'-binaphthyl, 6,6'-di-(dibenzo[b,d]furan-4-yl)-2,2'-bis-(2-hydroxyethoxy)-1,1'-binaphthyl and 6,6'-di-(dibenzo[b,d]thien-4-yl)-2,2'-bis-(2-hydroxyethoxy)-1,1'-binaphthyl.

12. The compound of claim 1, which is selected from the group consisting of 2,2'-{(6,6'-diphenyl[1,1'-binaphthalene]-2,2'-diyl)bis(oxy)}diacetic, 2,2'-{(6,6'-bis(1-naphthyl)phenyl[1,1'-binaphthalene]-2,2'-diyl)bis(oxy)}diacetic acid, 2,2'-{(6,6'-bis(2-naphthyl)phenyl[1,1'-binaphthalene]-2,2'-diyl)bis(oxy)}diacetic acid, 2,2'-{(6,6'-bis(9-phenanthryl)phenyl[1,1'-binaphthalene]-2,2'-diyl)bis(oxy)}diacetic acid, 2,2'-{(6,6'-bis(3-cyanophenyl)phenyl[1,1'-binaphthalene]-2,2'-diyl)bis(oxy)}diacetic acid, 2,2'-{(6,6'-bis(dibenzo[b,d]furan-4-yl)phenyl[1,1'-binaphthalene]-2,2'-diyl)bis(oxy)}diacetic acid, 2,2'-{(6,6'-bis(dibenzo[b,d]thien-4-yl)phenyl[1,1'-binaphthalene]-2,2'-diyl)bis(oxy)}diacetic acid, the corresponding methyl esters and the corresponding ethyl esters.

13. The compound of claim 1 having a purity of at least 95%, calculated as non-volatile organic matter.

14. The compound of claim 1, which is crystalline.

15. The compound of claim 1, where X is 1,2-ethandiyl.

16. The compound of claim 1, where X is $CH_2$—C(O)—.

17. The compound of claim 10, where the esters are $C_1$-$C_4$-alkylesters.

\* \* \* \* \*